US009387297B2

(12) United States Patent
Leone et al.

(10) Patent No.: US 9,387,297 B2
(45) Date of Patent: *Jul. 12, 2016

(54) VENTILATION SYSTEM WITH A TWO-POINT PERSPECTIVE VIEW

(71) Applicant: COVIDIEN LP, Mansfield, MA (US)

(72) Inventors: Kenneth Leone, Encinitas, CA (US); Marci Emily Palm, Trabuco Canyon, CA (US); Peter Doyle, Vista, CA (US)

(73) Assignee: COVIDIEN LP, Mansfield, MA (US)

( * ) Notice: Subject to any disclaimer, the term of this patent is extended or adjusted under 35 U.S.C. 154(b) by 404 days.

This patent is subject to a terminal disclaimer.

(21) Appl. No.: 13/967,920

(22) Filed: Aug. 15, 2013

(65) Prior Publication Data
US 2014/0034056 A1   Feb. 6, 2014

Related U.S. Application Data

(63) Continuation of application No. 12/768,649, filed on Apr. 27, 2010, now Pat. No. 8,539,949.

(51) Int. Cl.
*A61M 16/00* (2006.01)
*G09B 23/28* (2006.01)
(Continued)

(52) U.S. Cl.
CPC ....... *A61M 16/0051* (2013.01); *A61M 16/0057* (2013.01); *G09G 3/3426* (2013.01); *G09G 3/3648* (2013.01); *A61M 16/16* (2013.01); *A61M 2016/0027* (2013.01); *A61M 2202/025* (2013.01); *A61M 2202/0208* (2013.01); *A61M 2205/505* (2013.01); *A61M 2205/52* (2013.01);
(Continued)

(58) Field of Classification Search
CPC . A61M 16/00; A61M 16/0051; A61M 16/16; A61M 2016/0027; A61M 2202/0208; A61M 2202/025; A61M 2205/505; A61M 2205/52; A61M 2205/584; A61M 2205/8206; A61M 2205/8212; A61M 2205/8237; A62B 7/00; G09G 2300/0452; G09G 2320/064; G09G 2320/0646; G09G 2340/06; G09G 2360/145; G09G 3/3426; G09G 3/3648; G09B 23/00; G09B 23/28; G09B 23/288
USPC ............. 128/200.24, 201.27, 204.18, 204.21, 128/204.23, 204.22, 205.23
See application file for complete search history.

(56) References Cited

U.S. PATENT DOCUMENTS 4,227,645 A   10/1980   de La Farge et al.
4,323,064 A   4/1982    Hoenig et al.
(Continued)

FOREIGN PATENT DOCUMENTS

JP   08141085      4/1996
WO   WO 2005/013879   2/2005
(Continued)

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Annette Dixon

(57) ABSTRACT

The disclosure describes a novel approach for displaying information on a ventilator system. The disclosure describes a novel respiratory system including a primary display and system status display. Further, the disclosure describes a novel method for displaying ventilator information.

20 Claims, 11 Drawing Sheets

(51) Int. Cl.
    *G09G 3/34*       (2006.01)
    *G09G 3/36*       (2006.01)
    *A61M 16/16*      (2006.01)

(52) U.S. Cl.
    CPC .. *A61M 2205/584* (2013.01); *A61M 2205/8206* (2013.01); *A61M 2205/8212* (2013.01); *A61M 2205/8237* (2013.01); *G09B 23/288* (2013.01); *G09G 2300/0452* (2013.01); *G09G 2320/064* (2013.01); *G09G 2320/0646* (2013.01); *G09G 2340/06* (2013.01); *G09G 2360/145* (2013.01)

(56) References Cited

U.S. PATENT DOCUMENTS

| | | |
|---|---|---|
| 4,625,843 A | 12/1986 | Maltby et al. |
| 4,720,709 A | 1/1988 | Imamura et al. |
| 4,752,089 A | 6/1988 | Carter |
| 4,797,104 A * | 1/1989 | Laerdal ............ G09B 23/288 434/265 |
| 4,921,642 A | 5/1990 | LaTorraca |
| 4,954,799 A | 9/1990 | Kumar |
| 4,991,576 A | 2/1991 | Henkin et al. |
| 5,038,792 A | 8/1991 | Mault |
| 5,057,822 A | 10/1991 | Hoffman |
| 5,072,360 A | 12/1991 | Knorpp et al. |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,106 A * | 7/1994 | Lanpher ............ G09B 23/30 128/200.12 |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,372,545 A | 12/1994 | Noda et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,452,714 A | 9/1995 | Anderson et al. |
| 5,503,145 A | 4/1996 | Clough |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,570,688 A | 11/1996 | Cochran et al. |
| 5,590,648 A | 1/1997 | Mitchell et al. |
| 5,596,984 A | 1/1997 | O'Mahoney et al. |
| 5,611,327 A | 3/1997 | Teixeira Filho et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,678,539 A | 10/1997 | Schubert et al. |
| 5,687,717 A | 11/1997 | Halpern et al. |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,899,204 A | 5/1999 | Cochran |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,931,160 A | 8/1999 | Gilmore et al. |
| 5,934,274 A | 8/1999 | Merrick et al. |
| 5,991,883 A | 11/1999 | Atkinson |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,158,432 A | 12/2000 | Biondi et al. |
| 6,158,433 A | 12/2000 | Ong et al. |
| 6,161,539 A | 12/2000 | Winter |
| 6,178,905 B1 | 1/2001 | Dynes et al. |
| 6,220,245 B1 | 4/2001 | Takabayashi et al. |
| 6,269,812 B1 | 8/2001 | Wallace et al. |
| 6,273,088 B1 | 8/2001 | Hillsman |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,327,482 B1 | 12/2001 | Miyashita |
| 6,349,724 B1 | 2/2002 | Burton et al. |
| 6,357,438 B1 | 3/2002 | Hansen |
| 6,360,745 B1 | 3/2002 | Wallace et al. |
| 6,363,404 B1 | 3/2002 | Dalal et al. |
| 6,369,838 B1 | 4/2002 | Wallace et al. |
| 6,390,091 B1 | 5/2002 | Banner et al. |
| 6,392,158 B1 | 5/2002 | Caplet et al. |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,512,938 B2 | 1/2003 | Claure et al. |
| 6,515,683 B1 | 2/2003 | Wright |
| 6,517,492 B2 | 2/2003 | Koblanski |
| 6,543,449 B1 | 4/2003 | Woodring et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,591,835 B1 | 7/2003 | Blanch |
| 6,597,939 B1 | 7/2003 | Lampotang et al. |
| 6,622,726 B1 | 9/2003 | Du |
| 6,644,310 B1 | 11/2003 | Delache et al. |
| 6,668,824 B1 | 12/2003 | Isaza et al. |
| 6,670,950 B1 | 12/2003 | Chin et al. |
| 6,671,529 B2 | 12/2003 | Claure et al. |
| 6,675,801 B2 | 1/2004 | Wallace et al. |
| 6,686,716 B1 | 2/2004 | Predina et al. |
| 6,718,974 B1 | 4/2004 | Moberg |
| 6,725,447 B1 | 4/2004 | Gilman et al. |

(56) References Cited

U.S. PATENT DOCUMENTS

| | | |
|---|---|---|
| 6,738,079 B1 | 5/2004 | Kellarman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,782,888 B1 | 8/2004 | Friberg et al. |
| 6,796,305 B1 | 9/2004 | Banner et al. |
| 6,814,074 B1 | 11/2004 | Nadjafizadeh et al. |
| 6,834,647 B2 | 12/2004 | Blair et al. |
| 6,837,242 B2 | 1/2005 | Younes |
| 6,860,266 B2 | 3/2005 | Blike |
| 6,866,040 B1 | 3/2005 | Bourdon |
| 6,899,103 B1 | 5/2005 | Hood et al. |
| 6,956,572 B2 | 10/2005 | Zaleski |
| 6,960,854 B2 | 11/2005 | Nadjafizadeh et al. |
| 7,013,435 B2 | 3/2006 | Gallo et al. |
| 7,017,574 B2 | 3/2006 | Biondi et al. |
| 7,036,504 B2 | 5/2006 | Wallace et al. |
| 7,039,878 B2 | 5/2006 | Auer et al. |
| 7,040,057 B2 | 5/2006 | Gallant et al. |
| 7,040,318 B2 | 5/2006 | Dascher et al. |
| 7,040,321 B2 | 5/2006 | Gobel |
| 7,043,585 B2 | 5/2006 | Okin |
| 7,044,930 B2 | 5/2006 | Stromberg |
| 7,047,092 B2 | 5/2006 | Wimsatt |
| 7,062,251 B2 | 6/2006 | Birkett et al. |
| 7,077,131 B2 | 7/2006 | Hansen |
| RE39,225 E | 8/2006 | Isaza et al. |
| 7,117,438 B2 | 10/2006 | Wallace et al. |
| 7,162,296 B2 | 1/2007 | Leonhardt et al. |
| 7,201,166 B2 | 4/2007 | Blaise et al. |
| 7,210,478 B2 | 5/2007 | Banner et al. |
| 7,220,365 B2 | 5/2007 | Qu et al. |
| 7,255,103 B2 | 8/2007 | Bassin |
| 7,270,126 B2 | 9/2007 | Wallace et al. |
| 7,290,544 B1 | 11/2007 | Särelä et al. |
| 7,334,578 B2 | 2/2008 | Biondi et al. |
| 7,362,341 B2 | 4/2008 | McGuire et al. |
| 7,369,757 B2 | 5/2008 | Farbarik |
| 7,370,650 B2 | 5/2008 | Nadjafizadeh et al. |
| 7,395,216 B2 | 7/2008 | Rosenfeld et al. |
| 7,419,469 B2 | 9/2008 | Vacca |
| 7,428,902 B2 | 9/2008 | Du et al. |
| 7,433,827 B2 | 10/2008 | Rosenfeld et al. |
| 7,454,359 B2 | 11/2008 | Rosenfeld et al. |
| D583,948 S | 12/2008 | Hachimaru et al. |
| 7,460,959 B2 | 12/2008 | Jafari |
| 7,487,773 B2 | 2/2009 | Li |
| 7,502,221 B2 | 3/2009 | Fuller |
| 7,530,353 B2 | 5/2009 | Choncholas |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,997,269 B2 | 8/2011 | Yudkovitch et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,418,692 B2 | 4/2013 | Sanchez |
| 8,453,643 B2 | 6/2013 | Sanchez et al. |
| 8,457,706 B2 | 6/2013 | Baker, Jr. |
| 8,511,306 B2* | 8/2013 | Sanchez et al. |
| 8,539,949 B2* | 9/2013 | Leone ............... A61M 16/0051 128/200.24 |
| 8,792,949 B2 | 7/2014 | Baker, Jr. |
| 2002/0017299 A1 | 2/2002 | Hickle |
| 2002/0044059 A1 | 4/2002 | Reeder et al. |
| 2002/0080138 A1 | 6/2002 | Tarr |
| 2003/0062045 A1 | 4/2003 | Woodring et al. |
| 2003/0092381 A1 | 5/2003 | Buel et al. |
| 2003/0208465 A1 | 11/2003 | Yurko et al. |
| 2004/0030721 A1 | 2/2004 | Kruger et al. |
| 2004/0176983 A1 | 9/2004 | Birkett et al. |
| 2005/0016534 A1 | 1/2005 | Ost |
| 2005/0030309 A1 | 2/2005 | Gettman et al. |
| 2005/0039748 A1 | 2/2005 | Andrieux |
| 2005/0086612 A1 | 4/2005 | Gettman et al. |
| 2005/0108057 A1 | 5/2005 | Cohen et al. |
| 2005/0113668 A1 | 5/2005 | Srinivasan |
| 2005/0133027 A1 | 6/2005 | Elaz et al. |
| 2005/0139212 A1 | 6/2005 | Bourdon |
| 2005/0156933 A1 | 7/2005 | Lee et al. |
| 2005/0247311 A1 | 11/2005 | Vacchiano et al. |
| 2005/0288571 A1 | 12/2005 | Perkins et al. |
| 2006/0155183 A1 | 7/2006 | Kroecker et al. |
| 2006/0161748 A1 | 7/2006 | Wang et al. |
| 2006/0178911 A1 | 8/2006 | Syed et al. |
| 2006/0264762 A1 | 11/2006 | Starr |
| 2007/0017515 A1 | 1/2007 | Wallace et al. |
| 2007/0062529 A1 | 3/2007 | Choncholas et al. |
| 2007/0062532 A1 | 3/2007 | Choncholas |
| 2007/0062533 A1 | 3/2007 | Choncholas et al. |
| 2007/0077200 A1 | 4/2007 | Baker |
| 2007/0185390 A1 | 8/2007 | Perkins et al. |
| 2007/0199566 A1 | 8/2007 | Be'eri |
| 2007/0227537 A1 | 10/2007 | Bemister et al. |
| 2007/0272241 A1 | 11/2007 | Sanborn et al. |
| 2007/0272242 A1 | 11/2007 | Sanborn et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer |
| 2008/0078390 A1 | 4/2008 | Milne |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0183057 A1 | 7/2008 | Taube |
| 2008/0236585 A1 | 10/2008 | Parker et al. |
| 2008/0281167 A1 | 11/2008 | Soderberg |
| 2008/0295830 A1 | 12/2008 | Martonen et al. |
| 2009/0005651 A1 | 1/2009 | Ward et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0234328 A1 | 9/2009 | Cox et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |

(56) References Cited

U.S. PATENT DOCUMENTS

| | | |
|---|---|---|
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0018530 A1 | 1/2010 | Schindhelm et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0057618 A1 | 3/2010 | Spicer et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |

FOREIGN PATENT DOCUMENTS

| | | |
|---|---|---|
| WO | WO 2006/020862 | 2/2006 |
| WO | WO 2007/117716 | 10/2007 |
| WO | WO 2009/120607 A1 | 10/2009 |

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
PCT International Search Report and Written Opinion in International Application PCT/US2011/033460 mailed Oct. 12, 2011, 17 pgs.

(56) References Cited

OTHER PUBLICATIONS

PCT International Search Report and Written Opinion mailed Jun. 16, 2011; International Application No. PCT/US2010/058850, 16 pages.
PCT Partial International Search Report Date of Mailing Mar. 18, 2011, International Application No. PCT/US2010/058850, International Filing Date Dec. 3, 2010, 7 pgs.
U.S. Appl. No. 12/768,569, Notice of Allowance mailed Feb. 5, 2013, 8 pgs.
U.S. Appl. No. 12/768,569, Notice of Allowance mailed Mar. 25, 2013, 2 pgs.
U.S. Appl. No. 12/768,569, Notice of Allowance mailed Apr. 23, 2013, 2 pgs.
U.S. Appl. No. 12/768,569, Notice of Allowance mailed May 6, 2013, 2 pgs.
U.S. Appl. No. 12/768,649, Notice of Allowance mailed May 17, 2013, 6 pgs.
U.S. Appl. No. 12/768,649, Office Action mailed Feb. 12, 2013, 11 pgs.
U.S. Appl. No. 12/768,649, Office Action mailed Sep. 20, 2012, 12 pgs.
U.S. Appl. No. 12/768,656, Notice of Allowance mailed Jan. 28, 2013, 8 pgs.
U.S. Appl. No. 12/768,656, Notice of Allowance mailed Mar. 25, 2013, 2 pgs.
U.S. Appl. No. 12/768,656, Notice of Allowance mailed May 3, 2013, 2 pgs.
U.S. Appl. No. 12/775,779, Notice of Allowance mailed Dec. 18, 2012, 10 pgs.
U.S. Appl. No. 12/775,779, Office Action mailed Sep. 25, 2012, 20 pgs.
U.S. Appl. No. 12/775,788, Office Action mailed Sep. 25, 2012, 20 pgs.
U.S. Appl. No. 12/775,793, Advisory Action mailed Apr. 12, 2013, 2 pgs.
U.S. Appl. No. 12/775,793, Office Action mailed Jan. 30, 2013, 25 pgs.
U.S. Appl. No. 12/775,793, Office Action mailed Sep. 25, 2012, 21 pgs.
U.S. Appl. No. 29/299,059, Notice of Allowance emailed Nov. 23, 2011, 8 pgs.
U.S. Appl. No. 29/360,549, Notice of Allowance mailed May 10, 2011, 8 pgs.
U.S. Appl. No. 29/360,549, Notice of Allowance mailed Jun. 10, 2011, 3 pgs.
U.S. Appl. No. 12/775,793, Office Action mailed Jul. 5, 2013, 25 pgs.
U.S. Appl. No. 12/768,656, Notice of Allowance mailed Jul. 19, 2013, 2 pgs.
U.S. Appl. No. 12/775,793, Notice of Allowance mailed Oct. 25, 2013, 11 pgs.
Drager Medical, Instructions for Use Infinity Acute Care System, Evita Infinity V500 Ventilation Unit SW 1.n, 1st edition, Jun. 2008, Drager Medical, Germany, 276 pgs.

\* cited by examiner

VENTILATION SYSTEM WITH A TWO-POINT PERSPECTIVE VIEW

RELATED APPLICATIONS

This application is a continuation of U.S. application Ser. No. 12/768,649 filed on Apr. 27, 2010, entitled "VENTILATION SYSTEM WITH A TWO-POINT PERSPECTIVE VIEW," the entirety of which is hereby incorporated by reference.

INTRODUCTION

Many devices now use electronic graphical user interfaces (GUIs) as the primary user interface means instead of panels with mechanical elements such as knobs, buttons, switches etc. These GUIs are typically presented on a suitably-sized display (such as a flat panel display) in conjunction with a pointing or, as is increasingly common, a touch-sensitive display.

A drawback of electronic GUIs is the power consumption the displays require. Large and high resolution displays and support circuitry often consume excessive amounts of power, making them unattractive for use with battery-powered devices.

Yet another drawback related to the power consumption issue is that in order for an operator to interact with or obtain information from the device in any way, the electronic GUI must be powered on, even when the information needed is unrelated to the operation of the device. For example, a device may have a battery that can be charged from wall power when the device is turned off. If the electronic GUI is the only interface, then in order to simply determine the charge condition of the battery, the device must be turned on in order to power the electronic GUI. Further, if the electronic GUI is the only interface, then an operator must turn on the device when selecting a ventilator for use on patient, to determine the ventilator configuration, ventilation programs, ventilator identification information, and maintenance information.

One way that has been used to address this problem is to provide combinations of limited function alpha numeric displays, lamps and LEDs in addition to the primary display to manage ancillary or status information that should be provided to the operator. However, such ancillary user interface elements can not be reconfigured as they are built into their devices. Therefore, if different operators want to see different types of ancillary information, the only way to achieve this is to create different physical housings for each set of ancillary information desired by consumers.

Another drawback to currently utilized ventilator systems is that different ventilators are often configured differently, making it difficult for ventilator operators to quickly find and/or locate the physical components of the ventilator. During ventilation, the operator needs to understand the status of the ventilator in addition to the status of the patient to properly care for the patient. Current systems provide stickers or papers on the ventilator system to direct the operator to proper parts in an attempt to help alleviate this problem; however, these stickers and papers may fade or fall off the ventilator over time.

An additional drawback to currently utilized ventilator systems is that the increased specificity and wide variety of ventilator systems and programs makes it difficult for a ventilator operator to quickly choose a desired and/or proper ventilator. The ventilator operator may have a limited amount of time to determine if a ventilator provides the needed features, contains enough of the desired gas source, and/or is properly configured, charged, maintained, and/or serviced. Because ventilators are typically utilized in complicated environments, such as in intensive care units, the operator may have a limited amount of time to pick and completely understand a ventilator. The large number of differences between different ventilators increases the amount of time necessary for an operator to pick and completely understand a ventilator, which is an undesirable side-effect of ventilator variety and specialization.

SUMMARY

The disclosure describes a novel approach for displaying information on a ventilator system. The disclosure describes a novel respiratory system including a primary display and system status display. Further, the disclosure describes a novel method for displaying ventilator information.

In part, this disclosure describes a method for displaying ventilation information on a ventilation system. The method includes performing the following steps:
 a) displaying a first set of data on a primary display;
 b) controlling the primary display with a primary display controller;
 c) displaying a second set of data on a system status display;
 d) controlling the system status display with a ventilation control system; and
 e) displaying a two-point perspective view representing a physical configuration of a portion of the ventilation system as a part of at least one of the first set of data and the second set of data.

Yet another aspect of this disclosure describes a ventilation system that includes: a main housing; a gas delivery system in the main housing; a ventilation control system in the main housing that controls the gas delivery system and monitors one or more of a patient physiological parameter, operational parameters of the ventilation system and user-defined parameters; a primary display controller that generates a graphical user interface and that receives user inputs through the graphical user interface and delivers commands to the ventilation control system based on the inputs; a primary display housing removably attached to the main housing; a primary display in the primary display housing that presents the graphical user interface; and a system status display incorporated into the main housing that receives status data directly from the ventilation control system and the system status display displays a two-point perspective view representing a physical configuration of a portion of the ventilation system.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiment systems and methods described below and are not meant to limit the scope of the invention in any manner, which scope shall be based on the claims appended hereto.

DETAILED DESCRIPTION

Figure 1:
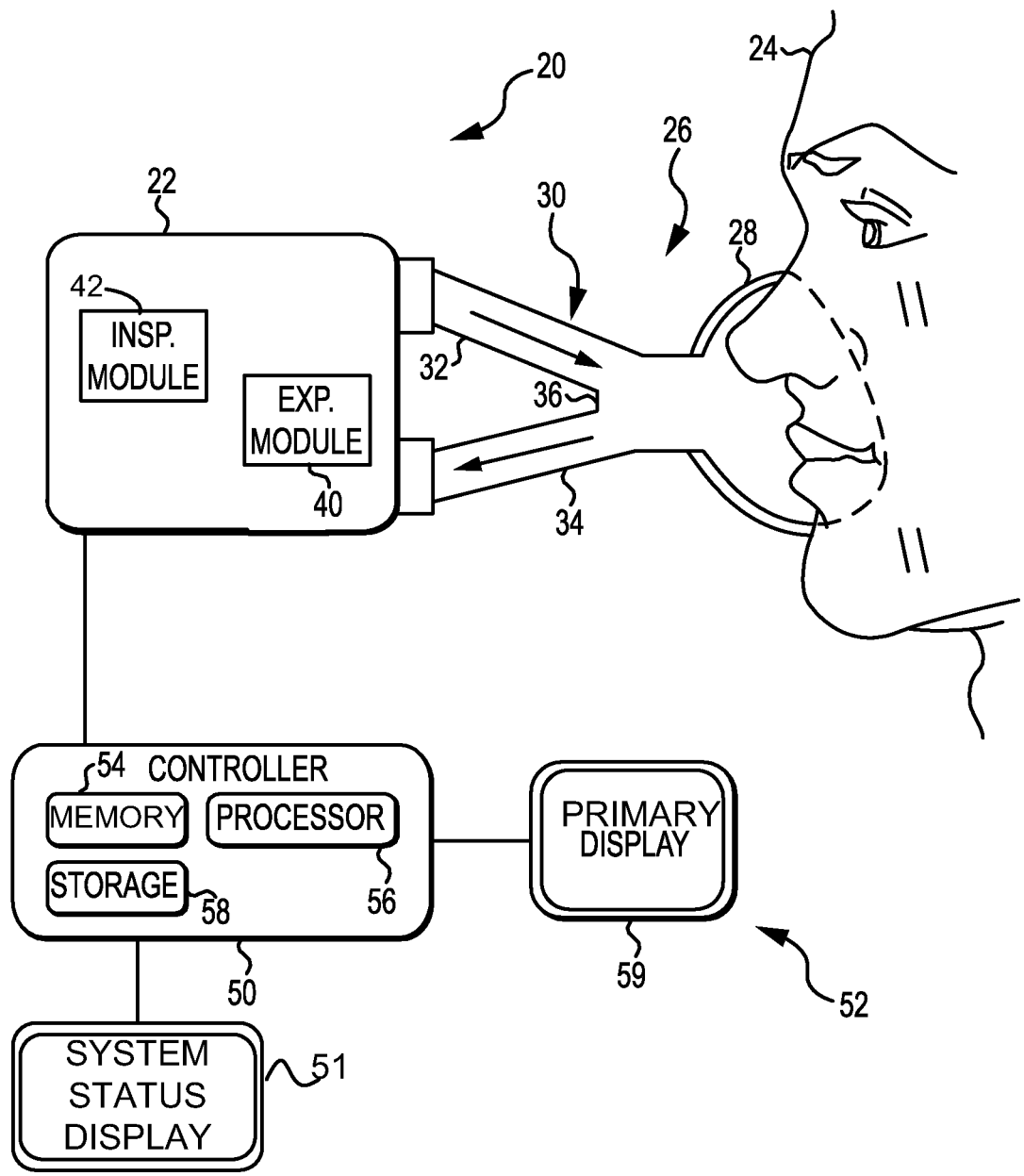
FIG. 1 illustrates an embodiment of a ventilator system including a primary removable display and a system status display.

This disclosure describes embodiments of novel display methods and of a system status display for use in devices such as medical ventilators that have an electronic graphical user interface (GUI) on a primary display device. The system status display (SSD) is a secondary display that has a more limited functionality than the electronic GUI on the primary display, and is provided primarily, if not solely, for the purpose of providing system status information to the operator.

Although the technology introduced above and discussed in detail below may be implemented for a variety of devices (and not just medical devices), the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients, different types of medical devices and any devices that use an electronic GUI presented on a primary display.

Medical ventilators are used to provide mixed gases that can be delivered in different modes of operation to a patient who may otherwise be unable to breathe sufficiently. This could include assisting a weakly breathing patient by reducing the work of breathing or by breathing for a patient that is unable to breathe. In modern medical facilities, pressurized air and oxygen sources are often available from wall outlets. Other, exotic gases such as helium, helium-oxygen mixtures (heliox), nitrogen and argon to name but a few, may also be used depending on the therapy being administered.

Medical ventilators monitor the delivery of breathing gas to the patient, may directly or indirectly monitor physiological parameters of the patient, and monitor the operation of the ventilator.

In the embodiments described herein, operators control the medical interface through an electronic GUI presented on a primary display, possibly in conjunction with one or more user input devices such as a thumbwheel, mouse, keyboard, or selector. As described above, typically, such a primary display is a large display which may be provided with touchscreen capability. The electronic GUI presented to the operator via this display allows the operator to view patient data in different forms, historical data, control the operation of the ventilator and change the therapy being provided to the patient. In an embodiment, every ventilator operation that can be performed by the ventilator can be accessed via the electronic GUI. Further, the electric GUI may or may not be removable from the ventilator housing.

Because of the computing power necessary to drive such a primary display, a separate GUI controller (which may alternatively be referred to as the primary display controller or graphics subsystem) is often used that is solely dedicated to running the primary display, interpreting user inputs received through the GUI, and passing that information on to the main ventilator controller that controls the actual gas delivery operations of the ventilator and any subsystems within the ventilator. Another function is to perform the computations and manipulations necessary to raw data provided by the main ventilator controller or discreet ventilator subsystems and turn them into the graphical presentations (waveforms, loops, monitored patient data, average values, etc.) shown on the GUI. For example, in an embodiment, the main ventilator controller monitors and outputs current parameters, which are then stored in memory to be accessed as needed by the GUI controller.

An example of one such subsystem is a battery control system. Typically, medical ventilators may be provided with one or more batteries to allow the ventilator to remain in operation without interruption while a patient is being transported between locations or during power loss. The battery system may include a monitoring and recharging subsystem that monitors the charge state and performance of the battery or batteries and keeps the batteries in a charged state.

Depending on the configuration of the ventilator other subsystems may be provided such as modules associated with gas sources, e.g., which gas sources are currently in use or modules associated with power management such as whether power is being delivered from a wall outlet or the battery system.

The SSD of the present disclosure is a secondary display that provides limited status information to the operator. In an embodiment, the SSD may not be interactive in any way, rather only providing status information in a predetermined or preselected format. Alternatively, some limited interaction may be provided through which a limited set of commands may be provided directly to the main breath delivery controller.

The SSD may be completely independent of the primary display and the GUI controller. One benefit of this architecture is that it allows the primary display and, thus the GUI, to be powered down or even completely removed from the ventilator while continuing to provide the operator with status of gas delivery to the patient and system status information. In another embodiment, the SSD is completely independent of the ventilation system. One benefit of this architecture is that it allows the ventilator to be powered down while continuing to provide the operator with system status information on the SSD. Having the SSD operational when the primary display and/or ventilator is powered down also has the benefit of allowing an operator to determine the status of various information without the need to power up/boot up the GUI controller or other non-essential systems. For example, during the selection of a ventilator system, a ventilator operator may refer to information (such as identification information, ventilation configuration features, a list of ventilator programs executable by the ventilator system, and/or maintenance information) provided by the SSD without having to power on the ventilator system or the electric GUI. Having quick and easy access to this information reduces the amount of time necessary for a ventilator operator to choose a desirable/proper ventilator.

In an embodiment, the SSD is a display located on the gas delivery system. In one embodiment, the SSD is a small, low-power display such as an LCD display to reduce the power demand of the SSD. In one embodiment, the SSD is always powered on when the ventilator is under battery power. In another embodiment, the SSD is always powered on when the ventilator is receiving external power. In yet another embodiment, when the ventilator is running on battery power, the SSD may power off and may be turned on using a separate SSD power switch (different from that controlling the primary display and electronic GUI and/or the ventilator). In one embodiment, the SSD or drive circuitry may be able to determine when the primary display is turned off or removed (if removable), during ventilation and may automatically turn on and remain on in such circumstances. In an alternative embodiment, the SSD may always be powered on when the ventilation is off but receiving external power. Further in another embodiment, the SSD or drive circuitry may be able to determine when the ventilator is turned off and may automatically turn the SSD on if the ventilator is receiving external power.

In an embodiment, when the SSD is on, the SSD may be programmable by the operator or manufacturer to meet local requirements or preferences. Likewise, the status data (that is data obtained from systems other than the GUI controller) displayed and the format of that display may also be user selectable.

In order to properly treat a patient, an operator must be familiar with the configuration of the ventilator system. However, various ventilators are configured in various ways, making it difficult for an operator to quickly find and locate components of a ventilation system. Accordingly, in one embodiment, the ventilator system described herein displays a two-point perspective view representing the physical configuration of a portion of the ventilator system on the SSD or electric GUI. Further, key components and ventilator system status may be displayed on this two-point perspective view representing the physical configuration of a portion of the ventilator system in the actual physical location of these components on the ventilator system. Accordingly, this display method decreases the amount of time necessary for a ventilator operator to locate various physical ventilator components on the ventilator system for providing proper patient ventilation.

FIG. 1 illustrates an embodiment of a ventilator system 20 (also referred to as ventilator 20) including a primary display 59, a system status display 51, a controller 50, and a pneumatic system 22 (also referred to as a gas delivery system 22). The ventilator system 20 further includes a main housing.

Ventilator 20 is connected to a human patient 24. Pneumatic system 22 (also referred to as a gas delivery system 22) delivers breathing gases to a patient 24 via the ventilation tubing system 26, which couples patient 24 to the pneumatic system 22 via physical patient interface 28 and ventilator circuit 30. The gas delivery system 22 is located in the main housing of ventilator 20. Ventilator circuit 30 could be a two-limb or one-limb circuit 30 for carrying gas mixture to and from the patient 24. In a two-limb embodiment as shown, a wye fitting 36 may be provided as shown to couple the patient interface 28 to the inspiratory limb 32 and the expiratory limb 34 of the circuit 30.

The present description contemplates that the patient interface 28 may be invasive or non-invasive, and of any configuration suitable for establishing a flow of breathing gas from the patient circuit 30 to an airway of the patient 24. Examples of suitable patient interface 28 devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. The inspiratory limb 32 receives a gas mixture from one or more gas sources controlled by one or more gas metering devices. The pneumatic system 22 may include a variety of other components, including other sources for pressurized air and/or oxygen, gas metering devices, accumulators, mixing modules, valves, sensors, tubing, filters, etc.

Controller 50 is operatively coupled with pneumatic system 22, signal measurement and acquisition systems, and an operator interface 52. The operator interface 52 may be provided to enable an operator to interact with the ventilator 20 (e.g., change ventilator settings, select operational modes, view monitored parameters, etc.). Controller 50 may include memory 54, one or more processors 56, storage 58, and/or other components of the type commonly found in command and control computing devices.

The memory 54 is non-transitory computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of non-transitory computer-readable media contained herein refers to a solid-state storage, it should be appreciated by those skilled in the art that non-transitory computer-readable storage media can be any available media that can be accessed by the processor 56. Non-transitory computer-readable storage media includes volatile and non-volatile, removable and non-removable media implemented in any method or technology for storage of information such as computer-readable instructions, data structures, program modules or other data. Non-transitory computer-readable storage media includes, but is not limited to, RAM, ROM, EPROM, EEPROM, flash memory, non-volatile memory, or other solid state memory technology, CD-ROM, DVD, or other optical storage, magnetic cassettes, magnetic tape, magnetic disk storage or other magnetic storage devices, or any other medium which can be used to store the desired information and which can be accessed by the processor 56.

The controller 50 issues commands to pneumatic system 22 in order to control the gas delivery provided to the patient 24 by the ventilator 20. The specific commands may be based on inputs received from patient 24, pneumatic system 22 and sensors, operator interface 52 and/or other components of the ventilator 20.

In the depicted example, operator interface 52 includes a primary display 59 that is touch-sensitive, enabling the primary display 59 to serve both as an input user interface and an output device. The primary display 59 is removable from the ventilator system 20. In an alternative embodiment, the primary display 59 is not removable from ventilator system 20. The primary display 59 can display any type of ventilation information, such as sensor readings, parameters, commands, alarms, warnings, and smart prompts (i.e., ventilator determined operator suggestions).

The primary display 59 is an electronic Graphical User Interface (GUI) that allows the operator to view patient data in different forms, view historical data, control the operation of the ventilator 20, and to change the therapy being provided to the patient. In an embodiment, every ventilator operation that can be performed by the ventilator 20 can be accessed via the electronic GUI or primary display 59. In another embodiment, a portion of the ventilator operations that can be performed by the ventilator 20 can be accessed via the electronic GUI of primary display 59.

In one embodiment, primary display 59 utilizes a separate GUI controller (not shown), which may alternatively be referred to as the primary display controller or graphics subsystem. A separate GUI controller may be utilized because the computing power necessary to drive primary display 59 is often solely dedicated to running the primary display, interpreting user inputs received through the GUI, and passing that information on to main ventilator controller 50 that controls the actual gas delivery operations of ventilator 20 and any subsystems within ventilator 20.

Primary display 59 also performs the computations and manipulations necessary to convert raw data, provided by main ventilator controller 50 or discreet ventilator subsystems, into the graphical presentations, such as waveforms, loops, monitored patient data, and/or average values for display on the GUI. This list is not limiting. Any suitable type of graphical presentation for a primary display 59 may be utilized. In one embodiment, the raw data and the generated graphical presentations are stored in memory to be accessed as needed by the GUI controller of primary display 59.

In this embodiment, ventilator 20 includes a battery control system (not shown). Medical ventilators may be provided with one or more batteries to allow ventilator 20 to remain in operation without interruption while a patient is being transported between locations or during power loss. In this embodiment, the ventilator 20 monitors the charge state and performance of the battery or batteries and keeps the batteries in a charged state. In this embodiment, the primary display 59 and/or SSD 51 is in communication with the battery control system and displays battery information received from the battery control system, such as battery use, battery performance, and battery charge levels.

In an alternative embodiment, the primary display includes a primary display battery control system that monitors the charge state and performance of the battery or batteries in ventilator system 20 and/or in the primary display 59 and keeps the batteries in a charged state. In this embodiment, the primary display 59 and/or SSD 51 independently communicates with the primary display battery control system and displays battery information received from the battery control system, such as battery use, battery performance, and battery charge levels.

Ventilator 20 further includes system status display (SSD) 51. The SSD 51 is a secondary display that provides limited status information to the operator. IN this embodiment, SSD 51 is not interactive in any way. SSD 51 displays status information in a predetermined or preselected format. In alternative embodiments, the SSD 51 provides for limited interactions, such as a set of commands provided directly to the controller 50. SSD 51 is completely independent of the GUI controller on the primary display 59. Accordingly, if the primary display 59 with the GUI controller fails, is disconnected, is removed from the ventilator 20, is powered off, or malfunctions, the SSD 51 still provides the operator with ventilator and patient information obtained directly from the controller 50. SSD 51 allows an operator to determine various information of ventilator system 20 and patient status information without having to power up/boot up, fix, or reattach primary display 59 with the GUI controller. In another embodiment, SSD 51 allows an operator to determine various information of ventilator 20 without having to power up/boot up the entire ventilator system 20.

For example, the SSD 51 of ventilator system 20 may be designed to display ventilator information that is helpful to a ventilator operator prior to use of ventilator 20. In this embodiment, the SSD 51 may display pre-use information, such as identification information, maintenance information, ventilator programs executable by ventilator 20 and/or ventilation configuration features. This information provides the ventilator operator with necessary information for selecting a proper and/or desirable ventilator 20 for each individual patient. Displaying this pre-use information on the SSD 51 allows information to be viewed quickly without having to power on the ventilator 20 and/or the primary display 59. Further, this SSD 51 groups all of the information necessary for selecting a ventilator 20 onto one screen, preventing the operator from having to navigate through several display screens to determine all of the information necessary for selecting a ventilator 20. Accordingly, the display of identification information, maintenance information, ventilator programs executable by ventilator 20 and/or ventilation configuration features on the SSD 51 decreases the amount of time necessary for a ventilator operator to select a proper and/or desirable ventilator 20. This time decrease is particularly desirable when ventilating a critical patient or when picking a ventilator 20 in a chaotic environment, such as an intensive care unit or in the field during a disaster.

The SSD 51 may display this pre-use information upon command, at all times, or in specific power or physical configurations. In one embodiment, the SSD 51 of ventilator 20 displays identification information, maintenance information, ventilator programs executable by ventilator 20 and/or ventilation configuration features continuously when the ventilator 20 is powered off/turned off but receiving power from an external power source. In another embodiment, the SSD 51 of ventilator 20 displays identification information, maintenance information, ventilator programs executable by ventilator 20 and/or ventilation configuration features upon user selection when the ventilation system is powered off but receiving power from a battery source. In yet another embodiment, the SSD 51 of ventilator 20 displays identification information, maintenance information, ventilator programs executable by ventilator 20 and/or ventilation configuration features upon user selection when the ventilation system is powered or turned on.

The type of pre-use information that is displayed may be determined by ventilator configuration, operator selection, operator input, and/or ventilator power or physical configuration. In one embodiment, the operator may input pre-use information into ventilator 20, such as identification information and maintenance information. In another embodiment, ventilator 20 may determine the pre-use information continuously and/or at upon configuration. For example, ventilator 20 may determine if the patient circuit 30 is in a neonate, a pediatric, or an adult configuration based on previous or current settings. In another embodiment, the make and model of ventilator 20 may be programmed into ventilator 20 upon configuration.

The identification information is any information that allows an operator to identify ventilator 20, such as an owner name, an owner address, an owner identification number, a model name, a model number, a brand name, a production date, and/or a manufacturer identification number to name only a few. In one embodiment, some of the identification information may be preconfigured into ventilator 20 or inputted by an operator. For instance, the model name, model number, and production date may be preconfigured into ventilator 20. In another example, the operator may input an owner name, an owner identification number, or other information valuable to the operator for identifying ventilator 20.

The maintenance information is any information that allows an operator to determine the maintenance, service, and/or performance status of ventilator 20. The maintenance information may include service information or test information.

Service information is any information relating to the service of ventilator 20. The service information may be related to previous services performed on ventilator 20 or to future services that needs to be performed on ventilator 20 for proper or desired maintenance of ventilator 20. The service information may include a service type, service date, service time, service reminder, preventative service date, future service information, and/or specific service information for individual components of ventilator 20, such as a gas source, oximeter, and/or capnograph. The future service information includes information relating to any already scheduled/planned future services for ventilator 20. The preventative service information includes reminders and/or warnings that let the operator know when future service should be performed and/or if a future service is due or past due.

In one embodiment, the SSD 51 displays the most recently performed service information, such as type of service, date of service, and time of service. In a further embodiment, the SSD 51 displays the number of hours ventilator 20 may be utilized to ventilate a patient before the next service is required. In an additional embodiment, the SSD 51 may further display the last service date for a gas source and the amount of time until the next service date for the gas source is necessary.

In one embodiment, the test information may be inputted or selected by the operator and/or service provider. In another embodiment, ventilator 20 may determine test information through a program executed by controller 50 or a primary display controller. In a further embodiment, the test information may be preconfigured into ventilator 20 and programmed to be displayed based on a preconfigured event and/or time duration.

The test information includes any information relating to any tests performed on ventilator 20 or any necessary or desirable future tests for ventilator 20. The test information may include, test type, test date, test time, test results, future test information, preventative test information, and/or specific test information for individual components of ventilator 20. In one embodiment, the test information includes the absence of a necessary test or test results. In another embodiment, the future test information includes information relating to any already scheduled/planned future tests for ventilator 20. The preventative test information may include reminders and/or warnings that let the operator know when future tests should be performed and/or if future tests are due or past due.

In another embodiment, the SSD 51 displays start-up test information. In yet another embodiment, the SSD 51 displays short self test and/or extended self test information, such as date, time, and results.

In one embodiment, the SSD 51 displays information relating to the most recently performed tests, such as type performed, date performed, and time performed. In a further embodiment, the SSD 51 displays the number of hours ventilator 20 may be utilized to ventilate a patient before the next test is required. In an additional embodiment, the SSD 51 may further display the last test date for a gas source and the amount of time until the next test for the gas source is necessary.

In one embodiment, the test information may be inputted or selected by the operator and/or service provider. In another embodiment, ventilator 20 may determine test information based on a program executed by controller 50 or primary display controller. In a further embodiment, the test information may be preconfigured into ventilator 20 and programmed to be displayed based on a preconfigured event and/or time duration.

The ventilator programs executable by ventilator 20 are programs or software that control and/or affect the ventilation of a patient being ventilated by ventilator 20. Different programs may be used to provide different types, or 'modes', of ventilation, such as volume controlled ventilation, pressure controlled ventilation, etc. Examples of ventilation modes used in the art include Continuous Positive Airway Pressure (CPAP), Proportional Assist Ventilation® Plus (PAV+) and Volume Ventilation Plus™ (VV+) to name only a few. These programs may be listed by name, abbreviation, and/or symbol.

Other ventilator programs utilized by the ventilator 20 further require physical ventilator configurations for proper use. Accordingly, the listing of these types of programs also informs the operator that these physical configurations are also present on the ventilator 20, such as neomode, autostart, ieSync, non-invasive neonatal CPAP (NIV Neo CPAP), Spontaneous Breath Trial Manager (SBT Manager), and/or Heliox to name only a few. For example, Heliox ventilation requires a specific valve for proper Heliox ventilation and NIV Neo CPAP requires a neonatal non-invasive patient interface. Accordingly, theses programs whether listed by name, abbreviation, and/or symbol represent that ventilator contains both the program/software and the physical ventilation system configuration and/or parts for properly executing these ventilator programs.

In one embodiment, all of the ventilator programs are displayed by the system status display 51. In another embodiment, a portion of the ventilator programs are displayed by the system status display 51. In one embodiment, the ventilator programs displayed by the system status display 51 are user selected. In another embodiment, the ventilator programs displayed by the SSD 51 are preconfigured.

The ventilation configuration features include features that describe how the ventilator 20 is physically configured, such as battery installation status, patient circuit configuration, humidifier configuration, compressor installation status, communication system installation status, external flow measurement system installation status, nebulizer installation status, and/or gas source installation status to name only a few. Battery installation status displayed on the system status display 51 informs the operator of what batteries are installed on the ventilator 20. In one embodiment, the battery installation status may further inform the operator what the charge level is of each installed battery. In another embodiment, the battery installation status may further inform the operator of which battery is charging or in use. Patient circuit configuration information displayed by the system status display 51 informs the operator if the patient circuit 30 of ventilator 20 is in a neonate, pediatric, or adult configuration. Humidifier configuration information displayed on the system status display informs the operator if a humidifier is utilized by ventilator 20 and if utilized, what kind of humidifier is utilized by the ventilation system. Compressor installation status information displayed by the SSD 51 informs the operator if a compressor is installed on ventilator 20. Gas source installation status information displayed by the system status display 51 informs the operator of what kinds of gas sources are installed on ventilator 20.

In one embodiment, SSD 51 is located on the housing of ventilator 20. In an embodiment, SSD 51 displays status information and is always on when ventilator 20 is provided with battery power and/or external power (e.g., when it is plugged into a wall socket). In the embodiment shown, the SSD 51 is a small, low-power display, such as an LCD display. In an alternative embodiment, SSD 51 is powered off unless an operator turns the SSD 51 on (with a different power switch from that controlling the primary display 59 and/or ventilator 20) when ventilator 20 is provided with battery power and/or external power. In another embodiment, SSD 51 has drive circuitry to determine when the primary display is turned off, disabled, failing or removed from ventilator 20 (e.g., such as for transport to conserve battery life) and automatically turns on for a portion of time. In this embodiment, SSD 51 may remain on. In another embodiment, SSD 51 remains on until the operator switches SSD 51 off, SSD 51 runs out of power, the primary display 59 is turned on, is fixed, or is reattached, and/or an external power source is utilized. In another embodiment, SSD 51 has drive circuitry to determine when the SSD is turned off or turned on.

In one embodiment, SSD 51 is programmable by the operator or manufacturer to meet local requirements or preferences. Further, status data (that is obtained from systems other than the GUI controller of the primary display 59) is displayed. In another embodiment, the format of the data displayed on the SSD 51 is selected by the operator or manufacturer.

In one embodiment, ventilator 20 may be configured to display a two-point perspective view representing a physical configuration of a portion of ventilation system 20. The two-point perspective illustration may be displayed by SSD 51 and/or primary display 59. In order to properly ventilate a patient, the operator needs to understand the status of the ventilator 20 in addition to the status of the patient. In order for the operator to fully understand the status of the ventilator 20, the operator must be able to locate and/or identify specific components of ventilator 20. The two-point perspective view representing the physical configuration of a portion of ventilator 20 provides the operator with a quick guide for locating and/or identifying specific components on ventilator 20.

Any suitable information can be displayed on the two-point perspective view representing the physical configuration of the portion of ventilator 20 for helping an operator understand the status of ventilator 20 and the location of key components of ventilator 20. In one embodiment, the two-point perspective view representing the physical configuration of the portion of ventilator 20 displays any available gas source, a location of any gas source on the ventilation system, gas source use status, any available power source, power source use status, compressor installation status, compressor use status, a location of any installed batteries on the ventilation system, any installed batteries use status, any installed batteries charge level, and/or installation status of any batteries. In another embodiment, the two-point perspective view representing the physical configuration of the portion of ventilator 20 displays the location of a gas delivery system, a compressor (if contained on ventilator 20), any type of installed gas source, an external power source, any installed battery, and/or a pressure gauge for a compressor (if contained on ventilator 20) as configured on ventilator 20.

In one embodiment, compressor installation status includes displaying if a compressor is contained in ventilator 20. In another embodiment, compressor use status displays if a compressor is being utilized or not utilized by ventilator 20. In one embodiment, battery installation status includes displaying if a battery is connected or not connected to ventilator 20. In another embodiment, battery use status displays if a connected battery is in use or not in use. In yet another embodiment, battery charge level displays if an installed battery is charged or not charged, charging or not charging, the charge level of an installed battery, and/or an estimate of the remaining amount of ventilator use time of an installed battery. The charge level of the battery may be depicted as a fuel gauge or as a time duration counting down the amount of useable amount of time left on a connected battery. In one embodiment, animation is utilized to show that any battery is charging or being utilized. In another embodiment, the animation is a ripple that moves upward if a battery is charging and moves downwards if a battery is being utilized denoting that the charge level of the battery to decrease.

The SSD 51 and/or primary display 59 may display a two-point perspective view representing the physical configuration of the portion of ventilator 20 upon command, at all times, or in specific power and/or physical configuration. In one embodiment, the SSD 51 and/or primary display 59 of ventilator 20 display the two-point perspective view representing the physical configuration of the portion of ventilator 20 continuously when ventilator 20 is powered off but receiving power from an external power source. In another embodiment, the SSD 51 or primary display 59 of ventilator 20 displays the two-point perspective view representing the physical configuration of the portion of ventilator 20 upon operator selection when the ventilation system is powered off but receiving power from a battery source. In yet another embodiment, the SSD 51 and/or primary display 59 of ventilator 20 displays the two-point perspective view representing the physical configuration of the portion of ventilator 20 upon user selection when the ventilation system is powered or turned on. In an alternative embodiment, the SSD 51 and/or primary display 59 of ventilator 20 displays the two-point perspective view representing the physical configuration of the portion of ventilator 20 at all times during ventilation of patient 24. In yet a further embodiment, the SSD 51 and/or primary display 59 of ventilator 20 displays the two-point perspective view representing the physical configuration of the portion of ventilator 20 when ventilator 20 is powered or turned on but not ventilating a patient.

In one embodiment, a portion of the information displayed on the two-point perspective view representing the physical configuration of the portion of ventilator 20 may be inputted or selected by the operator and/or service provider. In another embodiment, ventilator 20 may determine a portion of the information displayed on the two-point perspective view representing the physical configuration of the portion of ventilator 20 through a program executed by controller 50 or primary display controller. In a further embodiment, the information displayed on the two-point perspective view representing the physical configuration of the portion of ventilator 20 may be preconfigured into ventilator 20 and/or programmed to be displayed based on a preconfigured event and/or time duration.

Any of the information displayed on the SSD 51 or the primary display 59 may be depicted in any suitable manner utilizing icons, symbols, graphs, charts, text, light, light intensity, animation, and/or color.

Figure 2:
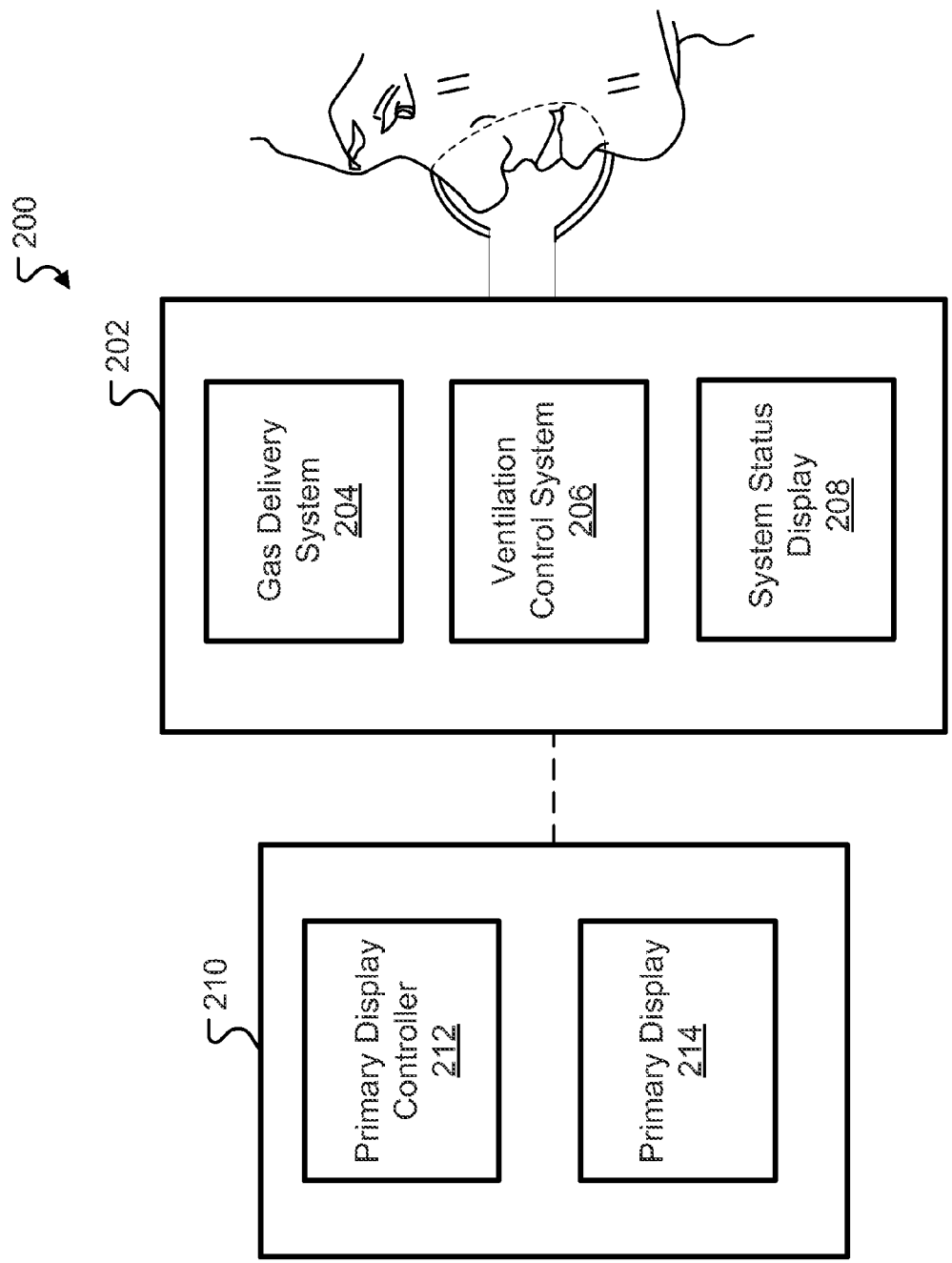
FIG. 2 illustrates an embodiment of a ventilator system including a primary removable display and a system status display.

Referring to FIG. 2, an embodiment of a ventilation system 200 is shown. Ventilation system 200 includes a main housing 202. The main housing 202 includes a gas delivery system 204, a ventilation control system 206, and a system status display (SSD) 208. The ventilation control system 206 controls the gas delivery system 204 and monitors one or more of a patient physiological parameter, operational parameters of the ventilation system 200, and user-defined parameters. In one embodiment, the ventilation control system 206 is located in the main housing 202. In an alternative embodiment, the ventilation control system 206 is located in a separate component independent of the main housing 202.

The system status display 208 receives status data directly from the ventilation control system 206 and displays the status data. In one embodiment, the system status display 208 includes a switch that turns the system status display 208 on and off, which is separate from the ventilation system 200's and the primary display's on/off switch. In another embodiment, at least one command is transmitted to the ventilation control system 206 via the system status display 208. In another embodiment, the at least one command is transmitted to the ventilation control system 206 via the system status display 208 upon user command. In one embodiment, the SSD 208 commands include power save, primary display 214 shut-down, system status display 208 shut-down, stand-by, charge, breath-type set-up, pressure support set-up, oxygen percent set-up, tidal volume set-up, breath-type change, pressure support change, oxygen percent change, and/or tidal volume change. All of the commands listed above are not limiting. Other suitable commands for controlling a ventilation system 200 may be added to the system status display 208.

The status data of the system status display 208 may display any suitable information, such as patient parameters, ventilation parameters, sensor readings, ventilator information, and/or calculated parameters. In one embodiment, the status data of the system status display 208 is selected from ventilator identification information, ventilator maintenance information, at least one ventilation program executable by the ventilation system 200 and/or at least one ventilation configuration feature. In another embodiment, system status display 208 displays a two-point perspective view representing a physical configuration of a portion of ventilation system 200. In a further embodiment, system status display 208 displays any available gas source, a location of any gas source on the ventilation system 200, gas source use status, any available power source, power source use status, compressor installation status, compressor use status, a location of any installed batteries on the ventilation system 200, any installed batteries use status, any installed batteries charge level, and/or installation status of any batteries on the two-point perspective view representing a physical configuration of a portion of ventilation system 200. In a further embodiment, system status display 208 displays the location of a gas delivery system, a compressor (if contained on ventilation system 200), any type of installed gas source, an external power source, any installed battery, and/or a pressure gauge for a compressor (if contained on ventilation system 200) as configured on ventilation system 200 on the two-point perspective view representing a physical configuration of a portion of ventilation system 200. All of this information may be depicted in any suitable manner, such as utilizing icons, graphs, charts, text, light, light intensity, animation, and/or color.

The identification information is any information that allows an operator to identify a ventilation system 200, such as an owner name, an owner address, an owner identification number, a model name, a model number, a brand name, a production date, and/or a manufacturer identification number. In one embodiment, some of the identification information may be preconfigured into ventilation system 200 or inputted by an operator.

The maintenance information is any information that allows an operator to determine the maintenance, service, and/or performance status of the ventilation system 200. The maintenance information may include service information or test information.

Service information is any information relating to the service of the ventilation system 200. The service information may be related to previous services performed on the ventilation system 200 or to future services that need to be performed on the ventilation system 200 for proper or desired maintenance of the ventilation system 200.

The test information is any information relating to any tests performed on the ventilation system 200 or any necessary or desirable future tests for the ventilation system 200. The test information may include, test type, test date, test time, test results, future test information, preventative test information, and/or specific test information for individual components of the ventilation system 200.

In one embodiment, the ventilator programs executable by ventilation system 200 are programs that control and/or affect the ventilation of a patient being ventilated by ventilation system 200. These programs may be listed by name, abbreviation, and/or symbol. In one embodiment, all of the ventilator programs are displayed by the system status display 208. In another embodiment, a portion of the ventilator programs are displayed by the system status display 208. In one embodiment, the ventilator programs displayed by the system status display 208 are operator selected. In another embodiment, the ventilator programs displayed by the system status display 208 are preconfigured.

In another embodiment, the ventilation configuration features include features that describe how the ventilation system 200 is physically configured, such as battery installation status, patient circuit configuration, humidifier configuration, compressor installation status, and/or gas source installation status. Battery installation status displayed on the system status display 208 informs the operator of what batteries are installed on the ventilation system 200.

In one embodiment, the battery installation status may further inform the operator of the charge level of each installed battery. Patient circuit configuration information displayed by the system status display 208 informs the operator if the patient circuit of ventilation system 200 is in a neonate, pediatric, or adult configuration. Humidifier configuration information displayed on the system status display 208 informs the operator if a humidifier is utilized by ventilation system 200 and if utilized, what kind of humidifier is utilized by the ventilation system 200. Compressor installation status information displayed by the system status display 208 informs the operator if a compressor is installed on ventilation system 200. Gas source installation status information displayed by the system status display 208 informs the operator of what kinds of gas sources are installed on ventilation system 200.

In one embodiment, compressor installation status includes displaying if a compressor is contained in ventilation system 200. In another embodiment, compressor use status displays if a compressor is being utilized or not utilized by ventilation system 200. In yet another embodiment, battery installation status includes displaying if a battery is connected to the ventilation system 200, displaying if a battery is disconnected from the ventilation system 200. In another embodiment, battery use status includes displaying if a battery is in use or not in use. In yet another embodiment, battery charge level includes displaying if a battery is charged, charge level of a battery and/or an estimate of battery life. The charge level of the battery may be depicted as a fuel gauge or as a time duration counting down the amount of useable time left on the battery.

Figure 8:
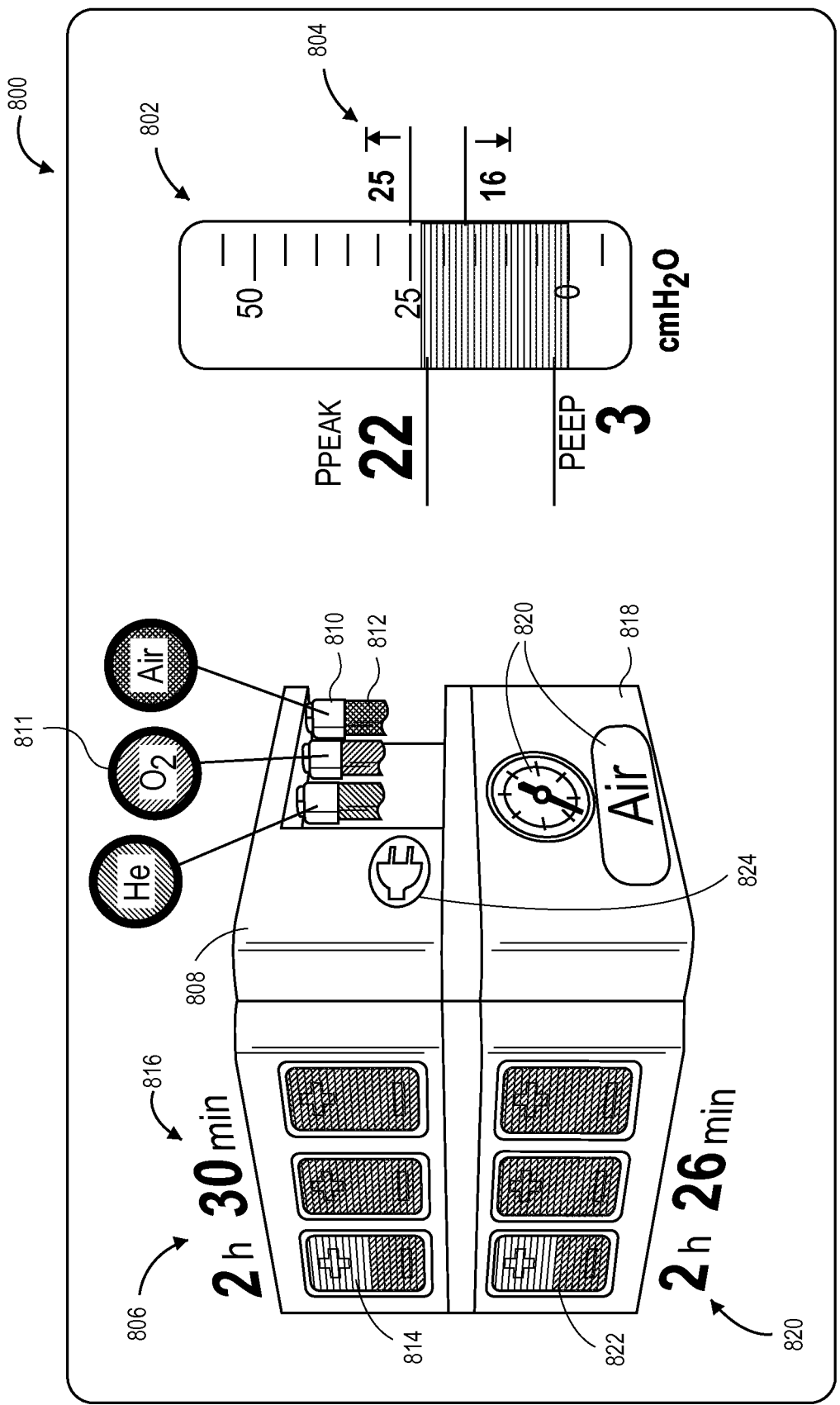
FIG. 8 illustrates an embodiment of a screen shot of a display on a ventilation system.
Figure 9:
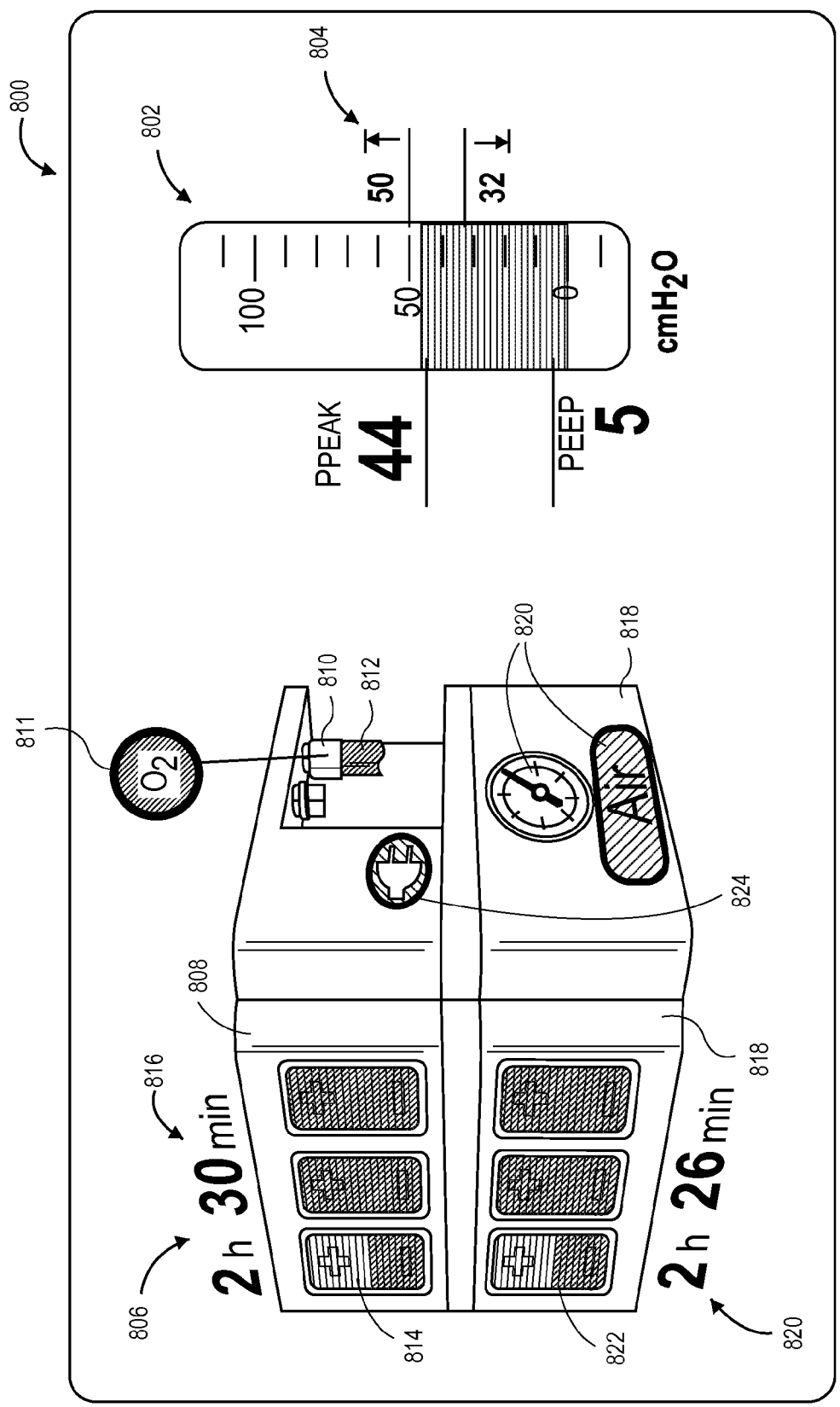
FIG. 9 illustrates an embodiment of a screen shot of a display on a ventilation system.

In one embodiment, a SSD 208 displays a manometer. The manometer displays the peak inspiratory pressure ($P_{PEAK}$), positive-end expiratory pressure (PEEP), and inspiratory pressure in thermometer-type display as illustrated in FIGS. 8 and 9. As the inspiratory pressure changes, the manometer may demonstrate this with the movement of the pressure meter up and down the vertical scale. In a further embodiment, the manometer may illustrate high and low alarm setting for the peak inspiratory pressure. In another embodiment, the pressure ranges of the manometer may change based on the patient setting (e.g. adult, pediatric, or neonate) of the ventilation system 200. For example, the embodiment of FIG. 8 displays the pressure range on a manometer for ventilating an infant and the embodiment of FIG. 9 displays an adult pressure range on a manometer for ventilating and adult or child. In another embodiment, the pediatric pressure range may be equal to the range displayed in FIG. 9.

Ventilation system 200 further includes a primary display housing 210. The primary display housing 210 is removably attached to the main housing 202. In an alternative embodiment, the primary display housing 210 is not removable from the main housing 202. In the embodiment as illustrated in FIG. 2, the primary display housing 210 includes a primary display controller 212 and a primary display 214. In an alternative embodiment, the primary display controller 212 is located in the main housing 202. In another embodiment, the primary display controller 212 is located in a separate component independent of the main housing 202 and the primary display housing 210.

Primary display 214 presents the graphical user interface. In one embodiment, the primary display 214 includes a mechanism that turns the primary display 214 on and off In another embodiment, the system status display 208, when in operation, uses at least less than 10%, more preferable less than 5% and even more preferably less than 2% of the power used by the primary display 214 when in operation. In yet another embodiment, the system status display 208, when in operation, uses at least less than 50% of the power used by the primary display 214 when in operation. In yet a further embodiment, the system status display 208, when in operation, uses at least less than 80% of the power used by the primary display 214 when in operation.

In an alternative embodiment, the system status display 208 has a low-power mode for conserving power consumption. The low-power mode reduces the amount of power consumed by the SSD 208 by at least 10%. In one embodiment, the low-power mode reduces the amount of power consumed by the SSD 208 by at least 50%. In another embodiment, the low-power mode reduces the amount of power consumed by the SSD 208 by at least 80%. In one embodiment, the SSD 208 enters the low-power mode when the primary display housing 210 is removed. In an additional embodiment, the SSD 208 is placed in a low-power mode when the primary display housing 210 is malfunctioning or disconnected. In another embodiment, the SSD 208 enters a low-power mode based on user command.

Primary display controller 212 generates the graphical user interface, receives operator inputs through the graphical user interface, and delivers commands to the ventilation control system 206 based on the operator inputs. In one embodiment, the primary display controller 212 places the primary display 214 in a safe disconnect mode to allow the primary display housing 210 to be removed. In an additional embodiment, the primary display controller 212 is placed in a low-power mode when the primary display housing 210 is removed. In another embodiment, the primary display controller 212 is turned off when the primary display housing 210 is removed. In yet another embodiment, the primary display controller 212 is turned off or placed in a low-power mode based on user command.

In one embodiment, the primary display 214 is suitable for displaying any of the information described above for the system status display 208, such as ventilation system 200 maintenance information, ventilation system 200 service information, ventilation system 200 programs executable by ventilation system 200, ventilation configuration features, and/or a two-point perspective view representing a physical configuration of a portion of ventilation system 200. In an alternative embodiment, primary display 214 display different information from the system status display 208.

Figure 3:
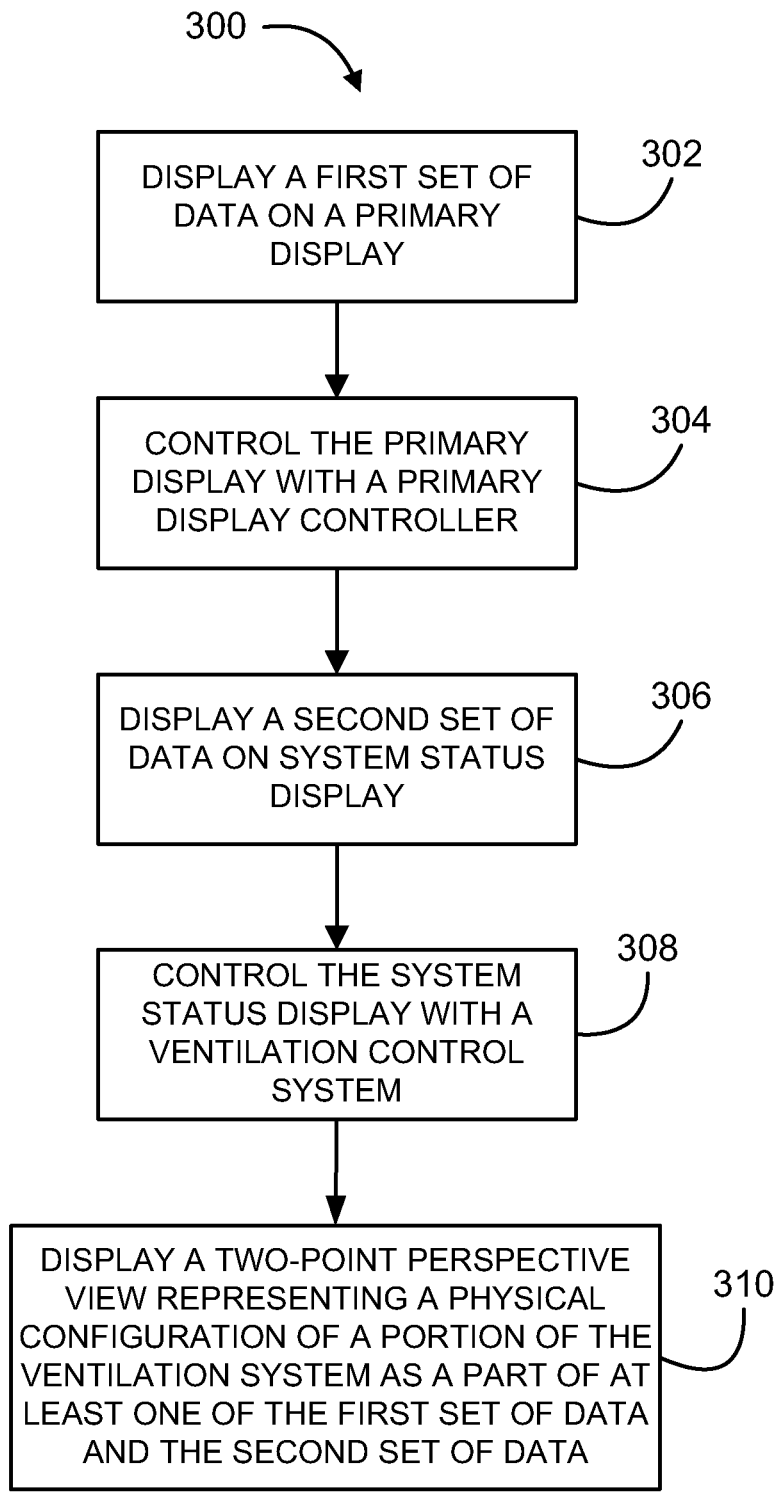
FIG. 3 illustrates an embodiment of a method for displaying ventilator information.

FIG. 3 illustrates an embodiment of a method 300 for displaying ventilator information on a ventilation system. As illustrated, method 300 performs a first display operation 302. First display operation 302 displays a first set of data on a primary display. In one embodiment, the first set of data includes ventilator status, available gas sources, utilized gas source or sources, available power sources, utilized power source, pressure trace of inspiratory pressure, positive-end expiratory pressure (PEEP), peak inspiratory pressure, battery system status, batteries in use, battery charge level, and/or a battery status. In another embodiment, the primary display is removable from a housing of the ventilation system.

As illustrated, method 300 performs a control operation 304. Control operation 304 controls the primary display with a processor. The processor may be part of a primary display controller. The control operation 304 determines what is displayed on the primary display.

Method 300 performs a second display operation 306. The second display operation 306 displays a second set of status data on the system status display. In one embodiment the second set of status data is different from the first set of status data. In another embodiment, the second set of status data includes ventilator maintenance information, ventilator identification information, ventilator programs executable by the ventilation system, ventilator configuration features, ventilator status, available gas sources, utilized gas source or sources, available power sources, utilized power source, pressure trace of inspiratory pressure, PEEP, peak inspiratory pressure, battery system status, batteries in use, battery charge level, and/or a battery status.

Method 300 performs a control operation 308. Control operation 308 controls the secondary display with a processor. The processor may be part of ventilation system or part of a system status display controller. The control operation 304 determines what is displayed on the system status display.

As illustrated, method 300 further performs a third display operation 310. Third display operation 310 displays a two-point perspective view representing a physical configuration of a portion of the ventilation system as part of at least one of the first set of data or the second set of data. In one embodiment, the first set of data on the system status display displays the two-point perspective view representing the physical configuration of a portion of the ventilation system. In an alternative embodiment, the second set of data on the primary display displays the two-point perspective view representing the physical configuration of a portion of the ventilation system. In another embodiment, both the first set of data and the second set of data displayed on the primary display and the system status display include the two-point perspective view representing the physical configuration of a portion of the ventilation system. The displayed two-point perspective view representing the physical configuration of the portion of the ventilation system may further include the location of a gas delivery system, the location of a compressor, the location of the location of a gas delivery system, the location of a compressor (if contained on ventilation system), the location of any type of installed gas source, the location of an external power source, the location of any installed battery, and/or the location of a pressure gauge for a compressor (if contained on ventilation system), any type of installed gas source, gas source use status, any available power source, power source use status, compressor installation status, compressor use status, any installed batteries use status, any installed batteries charge level, and/or installation status of any batteries. In one embodiment, the data displayed by third display operation 310 is the screen shot of a display illustrated in FIG. 8. In another embodiment, the data displayed by third display operation 310 is the screen shot of a display illustrated in FIG. 9.

In one embodiment, method 300 further performs a determination operation. The determination operation determines if the ventilation system is ventilating a patient and/or receiving power from an external source. If the determination operation determines that the ventilation system is ventilating a patient and/or receiving power from an external source, the determination operation has method 300 perform third display operation 310. If the determination operation determines that the ventilation system is not ventilating a patient and not receiving power from an external source, then the determination operation has method 300 perform first display operation 302 again.

In another embodiment, method 300 performs a monitoring operation. The monitoring operation monitors a compressor use status, a utilized power source, a battery charge level, and/or a kind of installed gas sources. In this embodiment, the monitored compressor use status, the utilized power source, the battery charge level, and/or the kind of installed gas source is displayed in a location on the two-point perspective view representing the physical configuration of the portion of the ventilation system corresponding to monitored parameters position/configuration on the actual ventilation system.

In yet another embodiment, method 300 performs a primary display determination operation. In this embodiment, the primary display is removable from the ventilation system. The primary display determination operation determines if the primary display is attached to the ventilation system. If the primary display determination operation determines that the primary display is attached to the ventilation system, then third display operation 310 displays a primary display attached to the ventilation system on the two-point perspective view representing the physical configuration of the portion of the ventilation system. If the primary display determination operation determines that the primary display is removed from the ventilation system, then third display operation 310 displays a primary display removed from the ventilation system on the two-point perspective view representing the physical configuration of the portion of the ventilation system. The attachment status of the primary display may be displayed though any suitable method, such as an icon, text, and/or a graphical picture.

Figure 4:
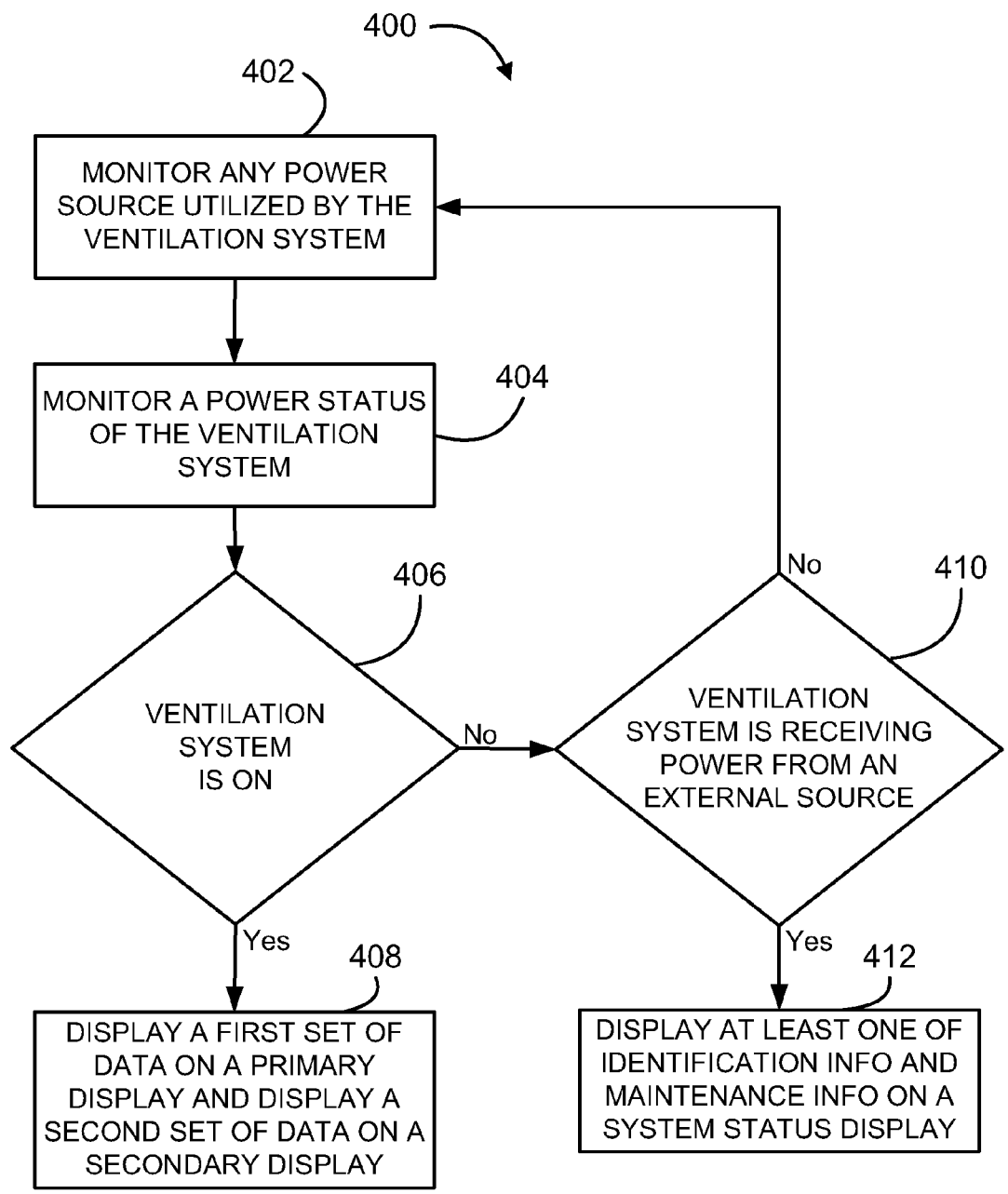
FIG. 4 illustrates an embodiment of a method for displaying ventilator information.

FIG. 4 illustrates an embodiment of a method 400 for displaying ventilator information on a ventilation system. As illustrated, method 400 performs a power source monitoring operation 402. Power source monitoring operation 402 monitors the power source utilized by the ventilation system. For instance, power source monitoring operation 402 monitors if the ventilation system is utilizing external power, such as AC power or internal power, such as one or more batteries.

Further, method 400 performs a power status monitoring operation 404. Power status monitoring operation 404 monitors whether the ventilation system is powered on or is powered off. In one embodiment, the power status monitoring operation 404 utilizes drive circuitry to monitor whether the ventilation system is powered off/turned on or is powered off/turned off. In another embodiment, the power status monitoring operation 404 utilizes a sensor for monitoring the position of the on/off switch of the ventilation system.

Next, method 400 performs a power status decision operation 406. Power status decision operation 406 determines if the ventilation system is turned on. If power status decision operation 406 determines that the ventilation system is turned on, power status decision operation 406 decides to have method 400 perform first display operation 408. If power status decision operation 406 determines that the ventilation system is turned off, power status decision operation 406 decides to have method 400 perform power source decision operation 410.

Method 400 performs a first display operation 408. First display operation 408 displays a first set of data on a primary display and displays a second set of data of a secondary display. In one embodiment, the first set of data and the second set of data are different. In another embodiment the first set of data and the second set of data may include ventilator status, available gas sources, utilized gas source or sources, available power sources, utilized power source, pressure trace of inspiratory pressure, PEEP, peak inspiratory pressure, battery system status, batteries in use, battery charge level, and/or a battery status. In one embodiment, the primary display is removable from the ventilation system.

Further, method 400 performs a power status decision operation 410. Power status decision operation 410 determines if the ventilation system is receiving power from an external power source. If power status decision operation 410 determines that the ventilation system is receiving power from an external source, power status decision operation 410 decides to have method 400 perform second display operation 412. If power status decision operation 410 determines that the ventilation system is not receiving power from an external source, power status decision operation 410 decides to have method 400 perform a power source monitoring operation 402 again.

As illustrated, method 400 performs a second display operation 412. Second display operation 412 displays at least one of ventilation system identification information and ventilation system maintenance information on the system status display. In one embodiment, second display operation 412 displays a date, a time, and a result of a most recently performed short self test on the ventilation system. In another embodiment, second display operation 412 further displays a date, a time, and a result of a most recently performed extended self test on the ventilation system. In a further embodiment, second display operation 412 further displays a most recent date and time the ventilation system received maintenance and a number of hours the ventilation system can be utilized to ventilate a patient until the ventilation system requires new maintenance. In one embodiment, the data displayed by second display operation 412 is the screen shot of a display illustrated in FIG. 10. In another embodiment, the data displayed by second display operation 412 is the screen shot of a display illustrated in FIG. 11.

The identification information includes any information that allows an operator to identify a ventilation system, such as an owner name, an owner address, an owner identification number, a model name, a model number, a brand name, a production date, and/or a manufacturer identification number. In one embodiment, some of the identification information may be preconfigured into ventilation system or inputted by an operator.

The maintenance information is any information that allows an operator to determine the maintenance, service, and/or performance status of the ventilation system. The maintenance information includes service information or test information. Service information is any information relating to the service of the ventilation system. The service information may be related to any previous services performed on the ventilation system or to any future services that need to be performed on the ventilation system for proper or desired maintenance of the ventilation system. The test information includes any information relating to any tests performed on the ventilation system or any necessary or desirable future tests for the ventilation system. The test information may include, test type, test date, test time, test results, future test information, preventative test information, and/or specific test information for individual components of the ventilation system.

In one embodiment, method 400 further performs a maintenance monitoring operation. In this embodiment, the monitoring operation monitors any maintenance performed on the ventilation system. The monitoring operation may further monitor when future maintenance is required on the ventilation system.

Figure 5:
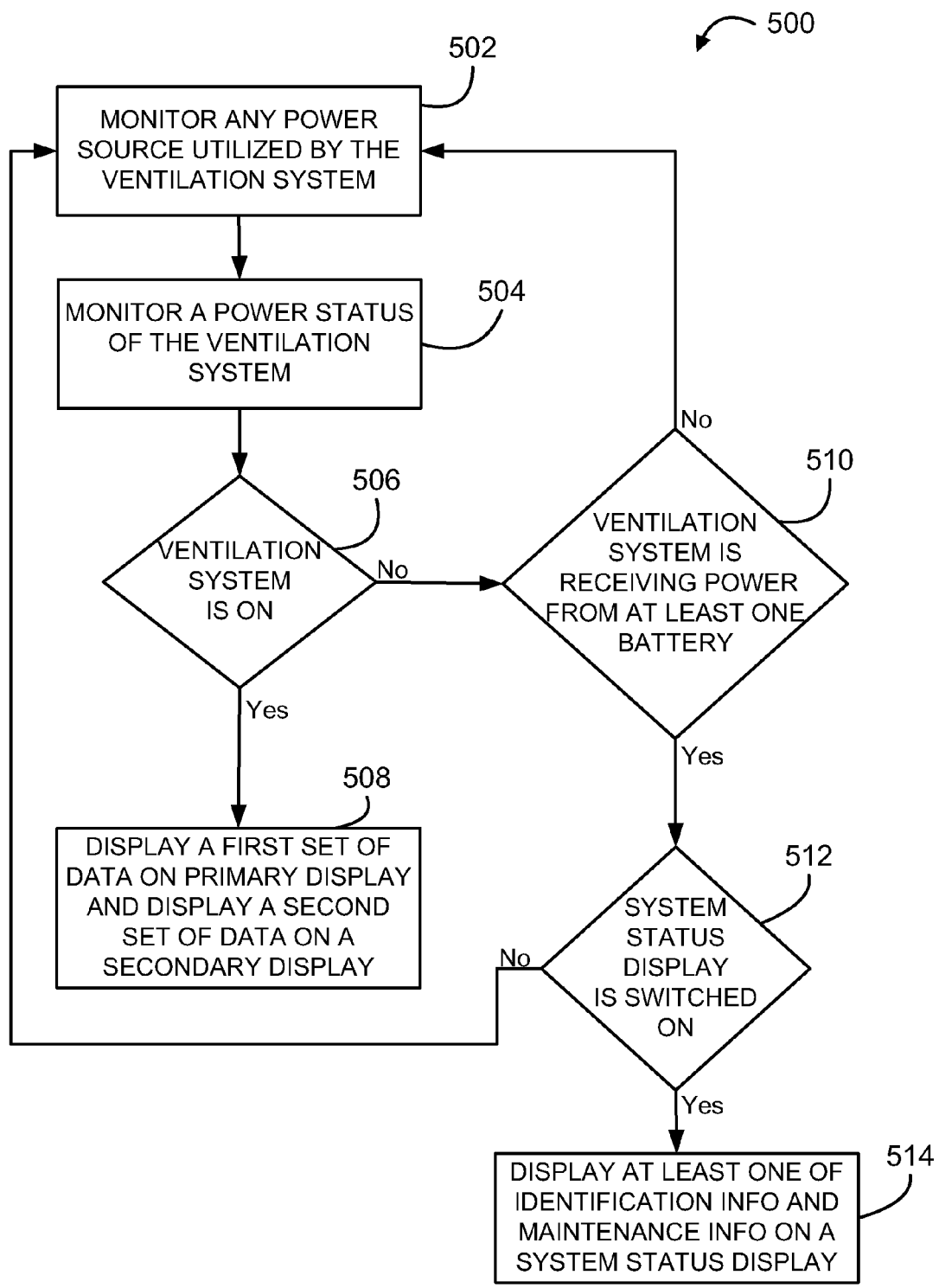
FIG. 5 illustrates an embodiment of a method for displaying ventilator information.

FIG. 5 illustrates an embodiment of a method 500 for displaying ventilator information on a ventilation system. As illustrated, method 500 performs a power source monitoring operation 502. Power source monitoring operation 502 monitors the power source utilized by the ventilation system. For instance, power source monitoring operation 502 monitors if the ventilation system is utilizing external power, such as AC power or internal power, such as one or more batteries.

Further, method 500 performs a power status monitoring operation 504. The power status monitoring operation 504 monitors whether the ventilation system is powered off/turned on or is powered off/turned off. In one embodiment, the power status monitoring operation 504 utilizes drive circuitry to monitor whether the ventilation system is powered on or is powered off. In another embodiment, the power status monitoring operation 504 utilizes a sensor for monitoring the position of the on/off switch of the ventilation system.

Next, method 500 performs a power status decision operation 506. Power status decision operation 506 determines if the ventilation system is turned on. If power status decision operation 506 determines that the ventilation system is turned on, power status decision operation 506 decides to have method 500 perform first display operation 508. If power status decision operation 506 determines that the ventilation system is turned off, power status decision operation 506 decides to have method 500 perform power source decision operation 510.

Method 500 performs first display operation 508. First display operation 508 displays a first set of data on a primary display and displays a second set of data of a secondary display. In one embodiment, the first set of data and the second set of data are different. In another embodiment the first set of data and the second set of data may include ventilator status, available gas sources, utilized gas source or sources, available power sources, utilized power source, pressure trace of inspiratory pressure, PEEP, peak inspiratory pressure, battery system status, batteries in use, battery charge level, and/or a battery status. In one embodiment, the primary display is removable from the ventilation system.

Further, method 500 performs a power source decision operation 510. Power source decision operation 510 determines if the ventilation system is receiving power from at least one battery. If power source decision operation 510 determines that the ventilation system is receiving power from at least one battery, power source decision operation 510 decides to have method 500 perform system status display status decision operation 512. If power source decision operation 510 determines that ventilation system is not receiving power from at least one battery, power source decision operation 510 decides to have method 500 perform the power source monitoring operation 502 again.

Method 500 performs system status display decision operation 512. System status display decision operation 512 determines if the system status display is switched on. In this embodiment, the system status display has a separate on/off switch from the ventilation system and the primary display. System status display decision operation 512 may utilize drive circuitry or a switch sensor to determine if the system status display is switched on. If system status display decision operation 512 determines that system status display is switched on, system status display decision operation 512 decides to have method 500 perform a second display operation 514. If system status display decision operation 512 determines that system status display is switched off, system status display decision operation 512 decides to have method 500 perform the power source monitoring operation 502 again.

As illustrated, method 500 performs a second display operation 514. Second display operation 514 displays at least one of ventilation system identification information and ventilation system maintenance information on the system status display. In one embodiment, the data displayed by second display operation 514 is the screen shot of a display illustrated in FIG. 10. In another embodiment, the data displayed by second display operation 514 is the screen shot of a display illustrated in FIG. 11.

The identification information includes any information that allows an operator to identify a ventilation system, such as an owner name, an owner address, an owner identification number, a model name, a model number, a brand name, a production date, and/or a manufacturer identification number. In one embodiment, some of the identification information may be preconfigured into ventilation system or inputted by an operator.

The maintenance information is any information that allows an operator to determine the maintenance, service, and/or performance status of the ventilation system. The maintenance information includes service information or test information. Service information is any information relating to the service of the ventilation system. The service information may be related to any previous services performed on the ventilation system or to any future services that need to be performed on the ventilation system for proper or desired maintenance of the ventilation system. The test information includes any information relating to any tests performed on the ventilation system or any necessary or desirable future tests for the ventilation system. The test information may include, test type, test date, test time, test results, future test information, preventative test information, and/or specific test information for individual components of the ventilation system. In one embodiment, the test information displayed on the system status display includes a date, a time, and a result of a most recent short self test and a most recent extended self test performed on the ventilation system. In another embodiment, the service information displayed on the system status display includes a date and a time of a most recent service performed on the ventilation system. In yet another embodiment, the service information displayed on the system status display includes an amount of time until a future service is required on the ventilation system.

In one embodiment, method 500 further performs a maintenance monitoring operation. In this embodiment, the monitoring operation monitors any maintenance performed on the ventilation system. The monitoring operation may further monitor when future maintenance is required on the ventilation system.

Figure 6:
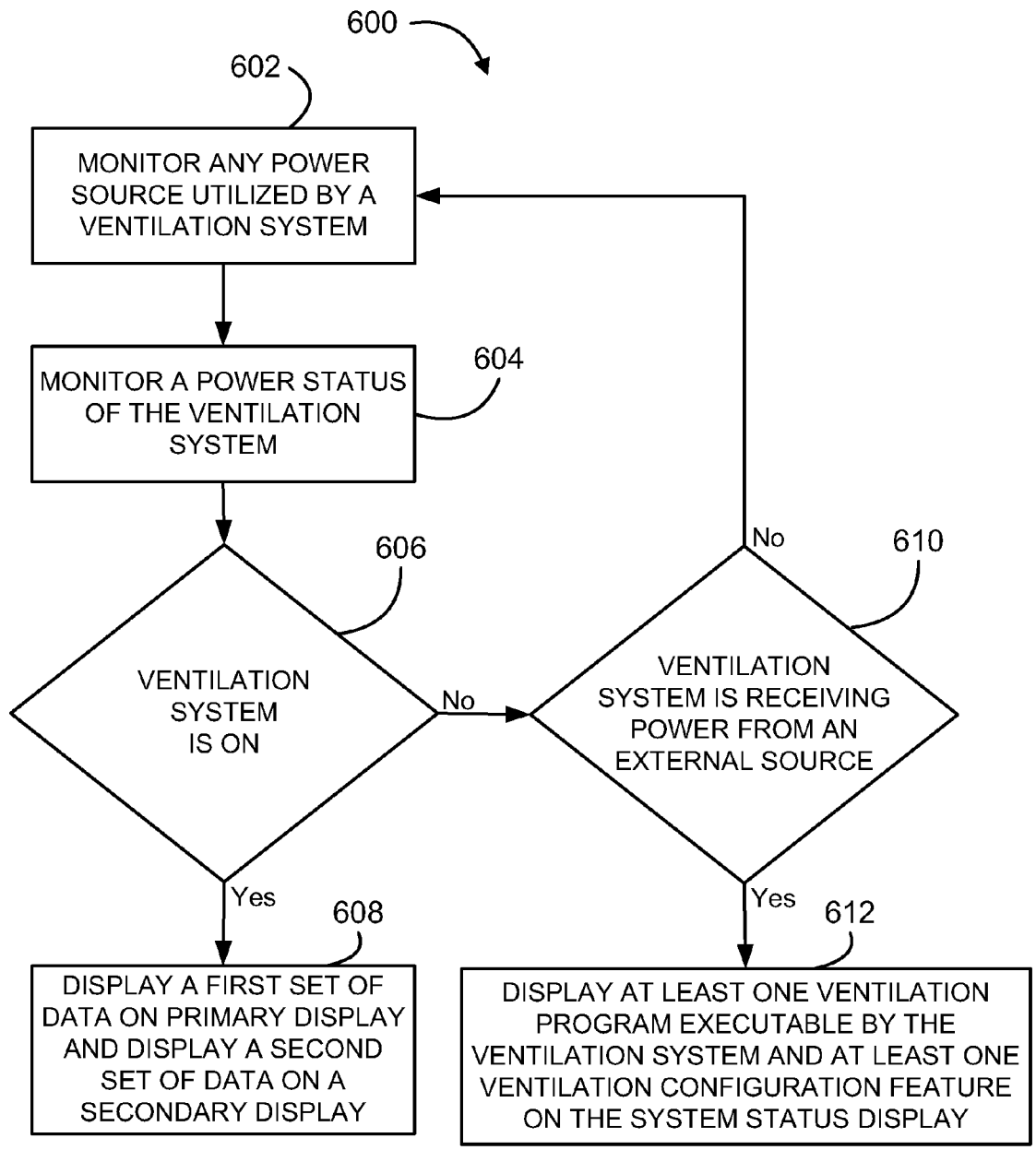
FIG. 6 illustrates an embodiment of a method for displaying ventilator information.

FIG. 6 illustrates an embodiment of a method 600 for displaying ventilator information on a ventilation system. As illustrated, method 600 performs a power source monitoring operation 602. Power source monitoring operation 602 monitors the power source utilized by the ventilation system. For instance, power source monitoring operation 602 monitors if the ventilation system is utilizing external power, such as AC power or internal power, such as one or more batteries.

Further, method 600 performs a power status monitoring operation 604. The power status monitoring operation 604 monitors whether the ventilation system is powered off/turned on or is powered off/turned off. In one embodiment, the power status monitoring operation 604 utilizes drive circuitry to monitor whether the ventilation system is powered on or is powered off. In another embodiment, the power status monitoring operation 604 utilizes a sensor for monitoring the position of the on/off switch of the ventilation system.

Next, method 600 performs a power status decision operation 606. Power status decision operation 606 determines if the ventilation system is turned on. If power status decision operation 606 determines that the ventilation system is turned on, power status decision operation 606 decides to have method 600 perform a first display operation 608. If power status decision operation 606 determines that the ventilation system is turned off, power status decision operation 606 decides to have method 600 perform a power source decision operation 610.

Method 600 performs a first display operation 608. First display operation 608 displays a first set of data on a primary display and displays a second set of data of a secondary display. In one embodiment, the first set of data and the second set of data are different. In another embodiment the first set of data and the second set of data may include ventilator status, available gas sources, utilized gas source or sources, available power sources, utilized power source, pressure trace of inspiratory pressure, PEEP, peak inspiratory pressure, battery system status, batteries in use, battery charge level, and/or a battery status. In one embodiment, the primary display is removable from a housing of the ventilation system.

Further, method 600 performs a power source decision operation 610. Power source decision operation 610 determines if the ventilation system is receiving power from an external power source. If power source decision operation 610 determines that the ventilation system is receiving power from an external source, power source decision operation 610 decides to have method 600 perform a second display operation 612. If power source decision operation 610 determines that ventilation system is not receiving power from an external source, power source decision operation 610 decides to have method 600 perform a power source monitoring operation 602 discussed above.

As illustrated, method 600 performs a second display operation 612. Second display operation 612 displays at least one ventilation program executable on the ventilation system and at least one ventilation configuration feature on the system status display. As discussed above, these programs or ventilation modes may be listed by name, abbreviation, and/or symbol. In one embodiment, all of the ventilator programs are displayed by the system status display. In another embodiment, a portion of the ventilator programs are displayed by the system status display. In one embodiment, the ventilator programs displayed by the system status display are user selected. In another embodiment, the ventilator programs displayed by the system status display are preconfigured. In one embodiment, the data displayed by second display operation 612 is the screen shot of a display illustrated in FIG. 10. In another embodiment, the data displayed by second display operation 612 is the screen shot of a display illustrated in FIG. 11.

The ventilation configuration features include features that describe how the ventilator is physically configured, such as battery installation status, patient circuit configuration, humidifier configuration, compressor installation status, and/or gas source installation status. Battery installation status displayed on the system status display informs the operator of what batteries are installed on the ventilator. In one embodiment, the battery installation status may further inform the operator of the charge level of each installed battery. Patient circuit configuration information displayed by the system status display informs the operator if the patient circuit of the ventilator is in a neonate, pediatric, or adult configuration. Humidifier configuration information displayed on the system status display informs the operator if a humidifier is utilized by the ventilation system and if utilized, what kind of humidifier is utilized by the ventilation system. Compressor installation status information displayed by the system status display informs the operator if a compressor is installed on the ventilation system. Gas source installation status information displayed by the system status display informs the operator of what kinds of gas sources are installed on the ventilation system.

In one embodiment, method 600 performs a ventilation configuration feature determination operation. The ventilation configuration feature determination operation determines at least one physical configuration feature of the ventilation system, such as battery installation status, patient circuit configuration, humidifier configuration, compressor installation status, gas source status, and/or ventilation programs. The ventilation configuration feature determination operation is performed prior to second display operation 612. In this embodiment, second display operation 612 displays the determined at least one physical configuration feature of the ventilation system.

In another embodiment, method 600 further performs a battery determination operation and a battery charge level determination operation. The battery determination operation determines if any batteries are installed on the ventilation system. The battery charge level operation determines the charge level of each installed battery. In this embodiment, the second display operation 612 displays the determined installed batteries and the charge level of any determined installed batteries.

In yet another embodiment, method 600 performs a patient circuit determination operation. The patient circuit determination operation determines the patient circuit configuration of the ventilation system. In this embodiment, second display operation 612 displays the determined patient circuit configuration.

In a further embodiment, method 600 performs a compressor determination operation. The compressor determination operation determines if the ventilation system comprises a compressor. In this embodiment, second display operation 612 displays the compressor installation status determined by compressor determination operation.

In yet a further embodiment, method 600 performs a humidifier determination operation. The humidifier determination operation determines if the ventilator contains a humidifier and if so, the kind of humidifier. In this embodiment, second display operation 612 displays the humidifier installation status determined by the humidifier determination operation.

In an additional embodiment, method 600 performs a gas source determination operation. The gas source determination operation determines each kind of gas source that is installed on the ventilation system. In this embodiment, second display operation 612 displays each kind of gas source installed on ventilation system as determined by the gas source determination operation.

In one embodiment, method 600 further performs a ventilation program determination operation. Ventilation program determination operation is performed before the second display operation 612. The ventilation program determination operation determines at least one ventilation program executable by the ventilation system to affect and/or control the ventilation of a patient being ventilated by the ventilation system. In this embodiment, the second display operation 612 displays the determined ventilation program.

Figure 7:
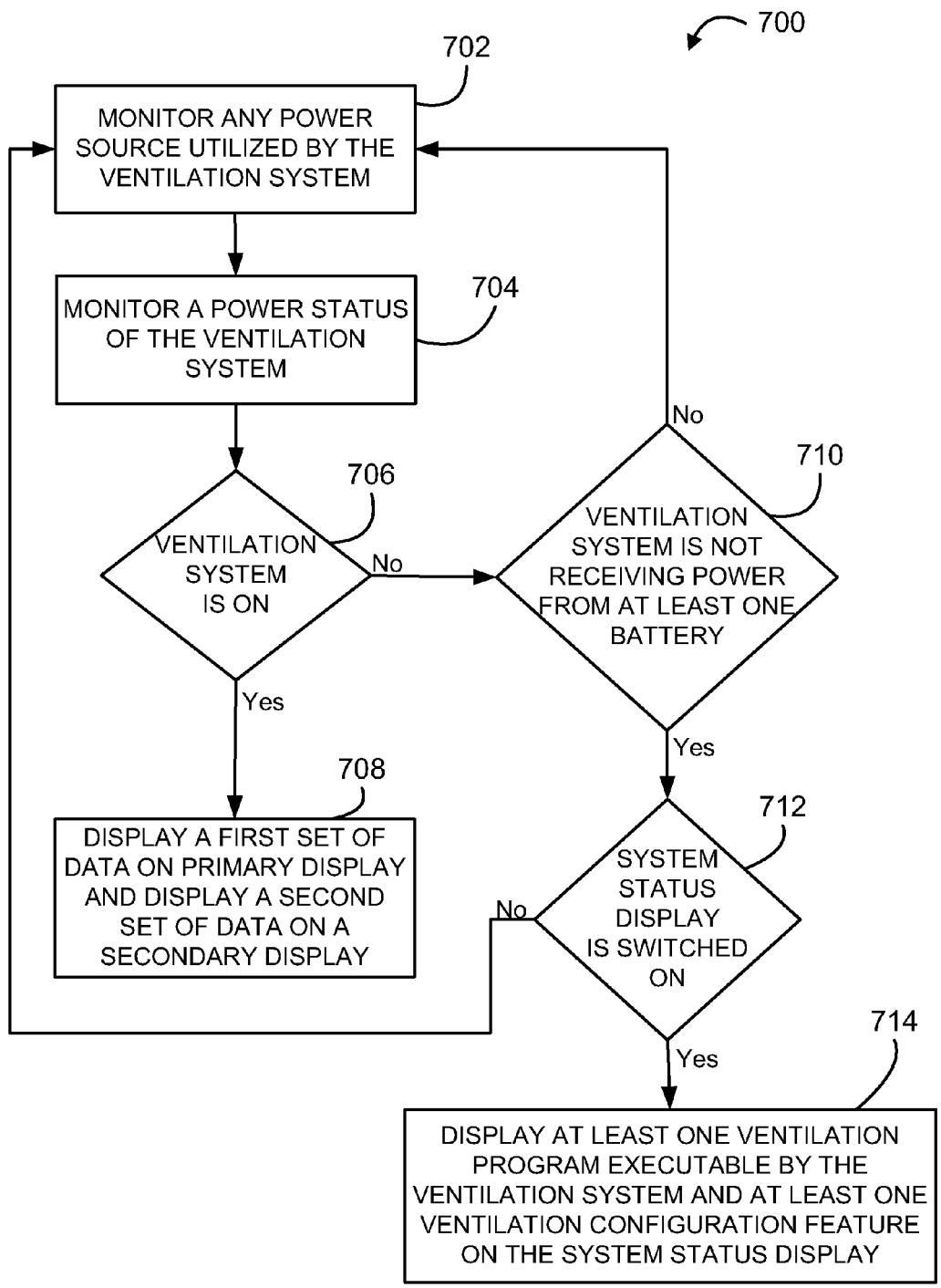
FIG. 7 illustrates an embodiment of a method for displaying ventilator information.

FIG. 7 illustrates an embodiment of a method 700 for displaying ventilator information on a ventilation system. As illustrated, method 700 performs a power source monitoring operation 702. Power source monitoring operation 702 monitors the power source utilized by the ventilation system. For instance, power source monitoring operation 702 monitors if the ventilation system is utilizing external power, such as AC power or internal power, such as one or more batteries.

Further, method 700 performs a power status monitoring operation 704. The power status monitoring operation 704 monitors whether the ventilation system is powered on or is powered off. In one embodiment, the power status monitoring operation 704 utilizes drive circuitry to monitor whether the ventilation system is powered off/turned on or is powered off/turned off. In another embodiment, the power status monitoring operation 704 utilizes a sensor for monitoring the position of the on/off switch of the ventilation system.

Next, method 700 performs a power status decision operation 706. Power status decision operation 706 determines if the ventilation system is turned on. If power status decision operation 706 determines that the ventilation system is turned on, power status decision operation 706 decides to have method 700 perform first display operation 708. If power status decision operation 706 determines that the ventilation system is turned off, power status decision operation 706 decides to have method 700 perform power source decision operation 710.

Method 700 performs first display operation 708. First display operation 708 displays a first set of data on a primary display and displays a second set of data of a secondary display. In one embodiment, the first set of data and the set of data are different. In another embodiment the first set of data and the second set of data may include ventilator status, available gas sources, utilized gas source or sources, available power sources, utilized power source, pressure trace of inspiratory pressure, PEEP, peak inspiratory pressure, battery system status, batteries in use, battery charge level, and/or a battery status. In one embodiment, the primary display is removable from a housing of the ventilation system.

Further, method 700 performs a power source decision operation 710. Power source decision operation 710 determines if the ventilation system is receiving power from at least one battery. If power source decision operation 710 determines that the ventilation system is receiving power from at least one battery, power source decision operation 710 decides to have method 700 perform system status display decision operation 712. If power source decision operation 710 determines that ventilation system is not receiving power from at least one battery, power source decision operation 710 decides to have method 700 perform the power source monitoring operation 702 again.

As illustrated, method 700 performs system status display decision operation 712. System status display decision operation 712 determines if the system status display is switched on. In this embodiment, the system status display has a separate on/off switch from the ventilation system and the primary display. System status display decision operation 712 may utilize drive circuitry or a switch sensor to determine if the system status display is switched on. If system status display decision operation 712 determines that system status display is switched on, system status display decision operation 712 decides to have method 700 perform a second display operation 714. If system status display decision operation 712 determines that system status display is not switched on, system status display decision operation 712 decides to have method 700 perform the power source monitoring operation 702 again.

Method 700 performs a second display operation 716. Second display operation 716 displays at least one ventilation program executable by the ventilation system and at least one ventilation configuration feature on the system status display. The ventilator programs executable by the ventilation system are programs that control and/or affect the ventilation of a patient being ventilated by the ventilation system. These programs may be listed by name, abbreviation, and/or symbol. In one embodiment, all of the ventilator programs are displayed by the system status display. In another embodiment, a portion of the ventilator programs are displayed by the system status display. In one embodiment, the ventilator programs displayed by the system status display are user selected. In another embodiment, the ventilator programs displayed by the system status display are preconfigured. In one embodiment, the data displayed by second display operation 716 is the screen shot of a display illustrated in FIG. 10. In another embodiment, the data displayed by second display operation 716 is the screen shot of a display illustrated in FIG. 11.

The ventilation configuration features include features that describe how the ventilator is physically configured, such as battery installation status, patient circuit configuration, humidifier configuration, compressor installation status, and/or gas source installation status. Battery installation status displayed on the system status display informs the operator of what batteries are installed on the ventilator. In one embodiment, the battery installation status may further inform the operator of the charge level of each installed battery. Patient circuit configuration information displayed by the system status display informs the operator if the patient circuit of the ventilator is in a neonate, pediatric, or adult configuration. Humidifier configuration information displayed on the system status display informs the operator if a humidifier is utilized by ventilation system and if utilized, what kind of humidifier is utilized by the ventilation system. Compressor installation status information displayed by the system status display informs the operator if a compressor is installed on the ventilation system. Gas source installation status information displayed by the system status display informs the operator of what kinds of gas sources are installed on the ventilation system.

In one embodiment, method 700 performs a ventilation configuration feature determination operation. The ventilation configuration feature determination operation determines at least one physical configuration feature of the ventilation system, such as battery installation status, patient circuit configuration, humidifier configuration, compressor installation status, gas source status, and/or ventilation programs. The ventilation configuration feature determination operation is performed prior to the system status display decision operation 712. In this embodiment, system status display decision operation 712 displays the determined at least one physical configuration feature of the ventilation system.

EXAMPLES

The following are embodiments of displays that could be shown on the SSD of a ventilation system.

The following are embodiments of a pressure trace or manometer that could be displayed on a SSD to allow an operator to determine from the SSD the ventilator's ability to support breath delivery to a patient.

FIGS. 8 and 9 illustrate an embodiment of a screen shot of a display on a ventilation system 800. In this example, the SSD displays a pressure trace or manometer 802 that indicates that pressure is transitioning between two points, such as PEEP and Peak Inspiratory Pressure ($P_{PEAK}$). As illustrated in FIGS. 8 and 9, the SSD displays a pressure trace 802 that provides an indication of the rise time of the pressure and the pressure levels. Further, as shown in the FIGS. 8 and 9, the SSD provides a continuous display of the minimum and peak inspiratory pressure levels.

As illustrated in FIGS. 8 and 9, the manometer 802 includes high and low peak inspiratory pressure alarms 804. The alarms 804 can be shown as a mark graphically on the manometer 802 or just listed as text beside the manometer 802. Additionally, the high and low peak inspiratory pressure alarm settings may be set by the operator. Further, while there are no fixed values for range on the manometer 802 for an adult, pediatric, or neonatal patient, the ventilator will have default settings based upon how the operator set-up the ventilator for the patient. However, the operator can override the default settings during the patient setup operation. FIG. 9 shows a manometer 802 with a default range setting for adult ventilation, while FIG. 8 shows a manometer 802 with a default range setting for neonate ventilation. Accordingly, the pressure ranges may vary depending upon if the ventilator is in an adult, pediatric, or neonate setting based on operator input or ventilator default settings.

The following are embodiments of the types of information that could be presented on an SSD to allow an operator to determine from the SSD the configuration of the ventilator system and more specifically where specific components are located on the ventilation system.

In this example, the SSD displays a two-point perspective view representing a physical configuration of a portion of the ventilation system 806. The two-point perspective view 806 mirrors the physical configuration of the ventilation system to allow an operator to be able to easily find and identify components on the actual ventilator system. In this example, as illustrated in FIGS. 8 and 9 the locations of a gas delivery system 808, a compressor 818, at least one available gas source 812, an external power source 824, any batteries 814 and 822, and a pressure gauge 820 for the compressor are illustrated on the two-point perspective view of a portion of the ventilation system 806. The two-point perspective view of a portion of the ventilation system 806 may illustrate other suitable ventilator information. As illustrated in FIGS. 8 and 9, the two-point perspective view of a portion of the ventilation system 806 further displays any available gas source 812, the type 811 of any available gas source 812, any gas source connectors 810, any available power sources 814, 822, and 824, utilization of any power sources 814, 822 (as illustrated in FIGS. 8 and 9), and 824 (as illustrated in FIG. 9), compressor installation status 818, compressor use status 820, battery use status 814 and 822, installed battery charge level 814, 822, 816, and 820 and battery installation status 814 and 822. The available gas sources 812 and any type of gas 811 as displayed in FIG. 9 include Air, Oxygen, and Helium 811. FIG. 8 shows three gas source connectors 810 with only Oxygen 811 as an installed available gas source 812. The power system information displayed in FIG. 8 shows that the ventilation system has an AC adapter 824, but is actively utilizing compressor and ventilator battery power 814 and 822 while FIG. 9 shows that the ventilation system is utilizing an AC adapter based on the highlighting of the AC adaptor icon 824. Additionally, both FIGS. 8 and 9 graphically depict the battery charge levels as a fuel gauge 814 and 822 and the amount of use time the batteries have left 816 and 820. Further the fuel gauge depiction of the battery charge level is color coded for easy interpretation 816 and 822. Further, the highlighting or shading of the compressor icon 820 in FIG. 9 illustrates that the ventilation system is actively utilizing the compressor 818.

In an alternative example, the display screen embodiments illustrated in FIGS. 8 and 9 are displayed on a primary display.

FIGS. 8 and 9 are examples of pre-use information that can be displayed on a SSD. The FIGS. Illustrate an embodiment of a screen shot of a system status display on a ventilation system 1000. The screen shot 1000 includes a two-point perspective view representing a physical configuration of a portion of the ventilation system 1002 and pre-use information. The pre-use information includes ventilation system identification information 1004, maintenance information, such as service information 1006 and test information 1008, a list of programs executable by the ventilation system that affect the ventilation of a patient 1012, and ventilator configuration information, such as patient circuit configuration 1010, gas source installation status 1014, compressor installation status 1016, and battery installation status 1018.

Figure 10:
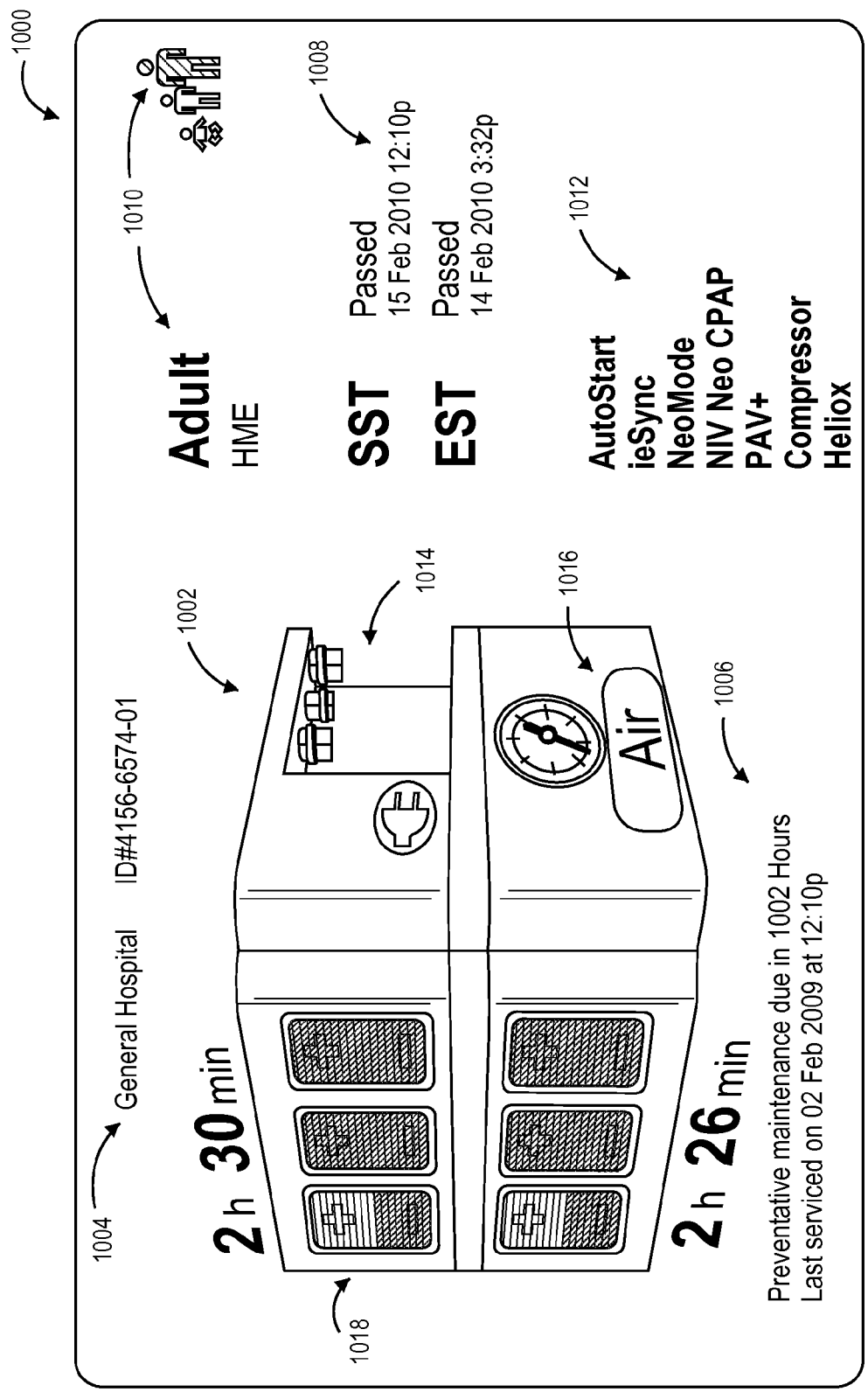
FIG. 10 illustrates an embodiment of a screen shot of a system status display.
Figure 11:
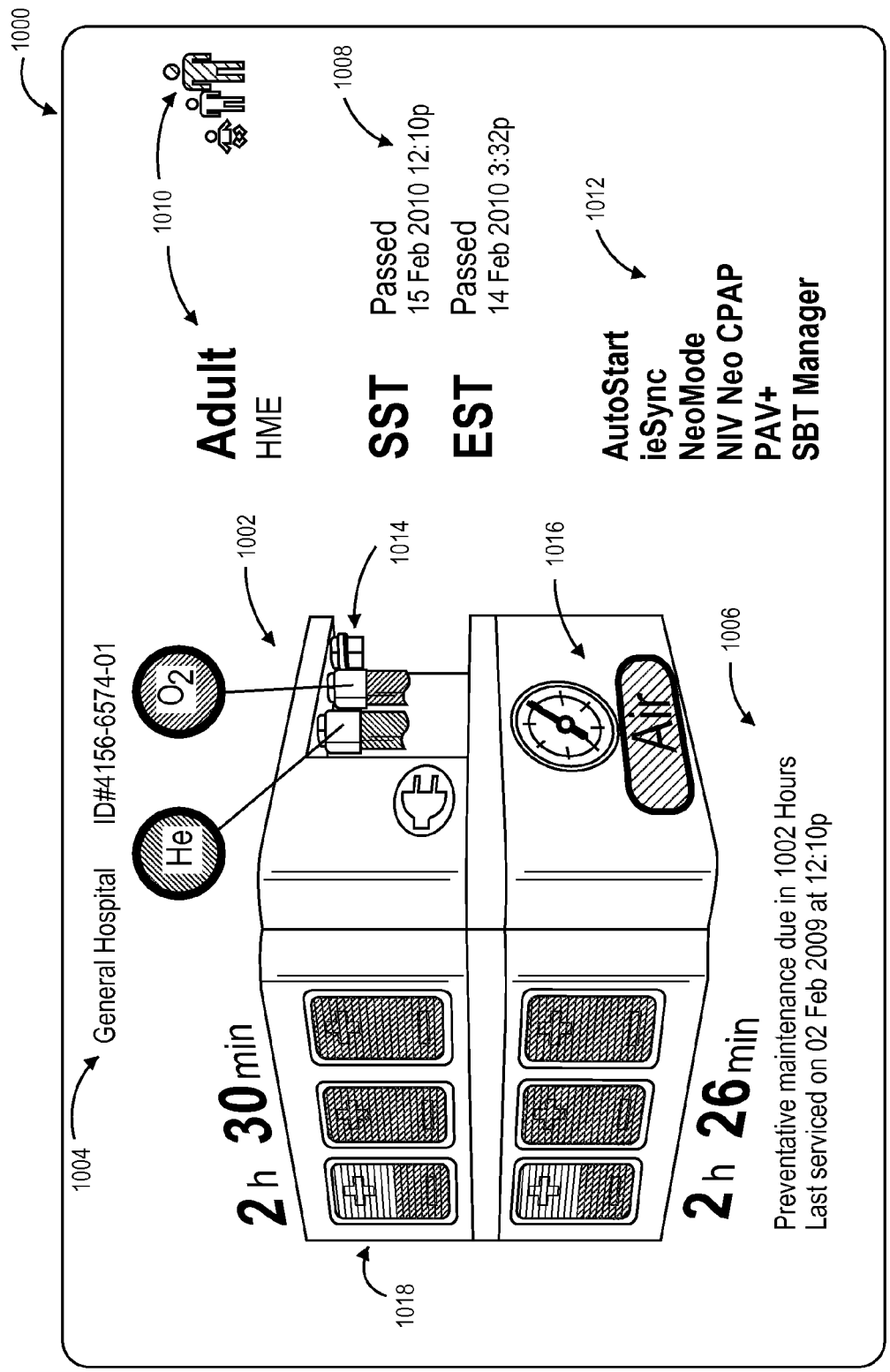
FIG. 11 illustrates an embodiment of a screen shot of a system status display.

As shown in FIGS. 10 and 11, the ventilation system identification information 1004 includes a hospital name and a hospital identification number. The ventilation system service information 1006 includes the amount of hours the ventilation system can be utilized to ventilate a patient before maintenance is recommended and a date and time of the last maintenance service, as shown in FIGS. 10 and 11. As illustrated in FIGS. 10 and 11, the ventilation system test information 1008 includes listing the date and time the last short self test and extended self test were performed and that the ventilation system passed these performed test. As illustrated in FIGS. 10 and 11, the list of programs or features executable or capable for use by the ventilation system 1012 are neomode, autostart, ieSync, NW Neo CPAP, SBT Manager, Compressor, Heliox, and PAV+. Further, FIGS. 10 and 11 illustrate the patient circuit configuration 1010 by listing the adult configuration and by highlighting an adult icon. As illustrated in FIG. 10, the gas source installation status 1014 shows that no gas sources are installed on this ventilation system. The gas source installation status 1014 displayed in FIG. 11 shows that helium and oxygen are installed on this ventilation system. The compressor installation status 1016 is illustrated by showing that this ventilation system includes a compressor. The compressor installation status 1016 in FIG. 11 further illustrates that the ventilation system is utilizing the compressor through the highlighting of the compressor icon and pressure dial movement. Additionally, as illustrated in FIGS. 10 and 11, the battery installation status 1018 shows that the ventilation system includes three pneumatic system batteries and three compressor batteries. The battery installation status 1018 further shows that two of the batteries are being utilized and further shows the amount of time the ventilation system can be utilized before the ventilation system runs out of battery power.

It will be clear that the systems and methods described herein are well adapted to attain the ends and advantages mentioned as well as those inherent therein. Those skilled in the art will recognize that the methods and systems within this specification may be implemented in many manners and, as such, are not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such a way as to be performed by a different module or method step without deviating from the overall disclosure. In other words, functional elements being performed by a single or multiple components, in various combinations of hardware, firmware, and software, and individual functions can be distributed among software applications. In this regard, any number of the features of the different embodiments described herein may be combined into one single embodiment and alternate embodiments having fewer than or more than all of the features described herein are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilation system comprising:
 a main housing;
 a gas delivery system in the main housing;
 a ventilation control system in the main housing that controls the gas delivery system and monitors one or more of a patient physiological parameter, operational parameters of the ventilation system and user-defined parameters;
 a system status display incorporated into the main housing that receives status data directly from the ventilation control system and the system status display displays a two-point perspective view depicting a physical configuration of a portion of the ventilation system, the two-point perspective identifying components currently attached to the ventilation system.

2. The ventilation system of claim 1, further comprising a removable primary display.

3. The ventilation system of claim 1, further comprising:
 a primary display controller that generates a graphical user interface and that receives user inputs through the graphical user interface and delivers commands to the ventilation control system based on the inputs; and
 a primary display that presents the graphical user interface.

4. The ventilation system of claim 1, wherein the two-point perspective view representing the physical configuration of the portion of the ventilation system further displays at least one of:
 an available gas source,
 a location of the available gas source on the ventilation system,
 a gas source use status,
 an available power source,
 a power source use status,
 a compressor installation status,
 a compressor use status,
 a location of installed batteries on the ventilation system,
 an installed batteries use status,
 an installed batteries charge level, and
 an installation status of at least one battery.

5. The ventilation system of claim 1, wherein the two-point perspective view representing the physical configuration of the portion of the ventilation system further displays at least one of a location on the ventilation system of the following:
 the gas delivery system,
 a compressor,
 a type of installed gas source,
 an external power source,
 an installed battery, and
 a pressure gauge for the compressor.

6. The ventilation system of claim 1, wherein the two-point perspective view representing the physical configuration of the portion of the ventilation system further displays a compressor installation status.

7. The ventilation system of claim 1, further comprising a compressor, wherein the two-point perspective view representing the physical configuration of the portion of the ventilation system further displays:
 a location of the compressor on the ventilation system;
 a location of a pressure gauge for the compressor on the ventilation system; and
 a compressor use status.

8. The ventilation system of claim 1, wherein the system status display displays the two-point perspective view representing the physical configuration of the portion of the ventilation system at all times unless the ventilator system is out of power.

9. The ventilation system of claim 1, wherein the two-point perspective view representing the physical configuration of the portion of the ventilation system further displays:
 an available gas source,
 a location of the available gas source on the ventilation system,
 a gas source use status,
 an available power source,
 a power source use status,
 a compressor installation status,
 a compressor use status,
 a location of installed batteries on the ventilation system,
 an installed batteries use status,
 an installed batteries charge level, and
 an installation status of at least one battery.

10. The ventilation system of claim 1, wherein the two-point perspective view representing the physical configuration of the portion of the ventilation system further displays a location on the ventilation system of the following:
 the gas delivery system,
 a compressor,
 a type of installed gas source,
 an external power source,
 an installed battery, and
 a pressure gauge for the compressor.

11. The ventilation system of claim 1, wherein the system status display further displays a pressure manometer.

12. A method for displaying ventilation information on a ventilation system comprising:
   displaying a first set of data on a primary display;
   displaying a second set of data on a system status display; and
   displaying a two-point perspective view depicting a physical configuration of a portion of the ventilation system as a part of at least one of the first set of data and the second set of data, the two-point perspective illustrating components currently attached to the ventilation system.

13. The method of claim 12, further comprising: controlling the primary display with a primary display controller, wherein the primary display is removable.

14. The method of claim 12, further comprising: controlling the system status display with a ventilation control system.

15. The method of claim 12, wherein the step of displaying the two-point perspective view representing the physical configuration of the portion of the ventilation system is only performed when the ventilation system is at least one of ventilating a patient and receiving external power.

16. The method of claim 12, wherein the step of displaying the two-point perspective view representing the physical configuration of the portion of the ventilation system further comprises displaying at least one of:
   an available gas source,
   a location of the available gas source on the ventilation system,
   a gas source use status,
   an available power source,
   a power source use status,
   a compressor installation status,
   a compressor use status,
   a location of installed batteries on the ventilation system,
   an installed batteries use status,
   an installed batteries charge level, and
   an installation status of at least one battery.

17. The method of claim 12, wherein the step of displaying the two-point perspective view representing the physical configuration of the portion of the ventilation system further comprises displaying a location of at least one of:
   a gas delivery system,
   a compressor,
   a type of installed gas source,
   an external power source,
   an installed battery, and
   a pressure gauge for the compressor.

18. The method of claim 12, further comprising,
   monitoring a configuration of the ventilation system before displaying the second set of data,
   wherein the two-point perspective view representing the physical configuration of the portion of the ventilation system is part of the second set of data.

19. The method of claim 12, further comprising:
   monitoring a compressor use status; and
   displaying the compressor use status in a location on the two-point perspective view representing the physical configuration of the portion of the ventilation system corresponding to a location of a pressure gauge on a compressor in the physical configuration of the ventilation system.

20. The method of claim 12, further comprising:
   monitoring a power source for the ventilation system; and
   displaying a utilized power source in a location on the two-point perspective view representing the physical configuration of the portion of the ventilation system corresponding to the physical configuration of the ventilation system.

* * * * *